United States Patent
Ishihara et al.

(10) Patent No.: US 8,198,445 B2
(45) Date of Patent: Jun. 12, 2012

(54) PHOSPHORAMIDE COMPOUND, METHOD FOR PRODUCING THE SAME, LIGAND, COMPLEX, CATALYST AND METHOD FOR PRODUCING OPTICALLY ACTIVE ALCOHOL

(75) Inventors: Kazuaki Ishihara, Nagoya (JP); Manabu Hatano, Nagoya (JP); Takashi Miyamoto, Nagoya (JP)

(73) Assignees: National University Corporation Nagoya University, Nagoya-shi (JP); Sekisui Medical Co., Ltd., Tokyo (JP)

( * ) Notice: Subject to any disclaimer, the term of this patent is extended or adjusted under 35 U.S.C. 154(b) by 160 days.

(21) Appl. No.: 12/530,287

(22) PCT Filed: Feb. 19, 2008

(86) PCT No.: PCT/JP2008/052779
§ 371 (c)(1),
(2), (4) Date: Nov. 25, 2009

(87) PCT Pub. No.: WO2008/111371
PCT Pub. Date: Sep. 18, 2008

(65) Prior Publication Data
US 2010/0113786 A1 May 6, 2010

(30) Foreign Application Priority Data

Mar. 9, 2007 (JP) ................................. 2007-061030

(51) Int. Cl.
*C07F 9/28* (2006.01)
*C07F 9/02* (2006.01)
*C07F 15/00* (2006.01)
(52) U.S. Cl. ........................... 546/22; 548/402; 548/413
(58) Field of Classification Search ........................ None
See application file for complete search history.

(56) References Cited

FOREIGN PATENT DOCUMENTS
JP          2006 35125        2/2006

OTHER PUBLICATIONS

F. Zaragoza Dorwald, Side Reactions in Organic Synthesis; A Guide to Successful Synthesis Design, Wiley-VCH, Weinheim, Preface, p. IX (2005).*
Wikipedia: Definition for "Carbonyl" [online]. [retrieved on Sep. 26, 2011]. Retrieved from the Internet:<http://en.wikipedia.org/wiki/Carbonyl>.*
Palmer, Matthew J. et al., "The Use of Phosphinamide N-Protecting Groups in the Diastereoselective Reduction of Ketones.", Tetrahedron Letters, Pergamon, vol. 38, No. 13, pp. 2315-2316, (1997).
Palmer, Matthew J. et al., "The Use of Phosphinamide N-Protecting Groups in the Diastereoselective Reduction of Ketones.", Tetrahedron, Pergamon, vol. 54, No. 30, pp. 8827-8840, (1998).
Savignac, P. et al., Phosphoramides ω Amines. I. Synthesis of Diaminoethanes and Diaminopropanes, Journal of Organometallic Chemistry, vol. 60, No. 1, pp. 103-113, (1973) (with English abstract).
Li, Kangying et al., "Asymmetric carbonyl reduction with borane catalyzed by chiral phosphinamides derived from L-amino acid", Tetrahedron: Asymmetry, Pergamon, vol. 14, No. 1, pp. 95-100, (2003).
Zhou, Zheng-Hong et al., "Synthesis of New Chiral Phosphorus Compounds as Ligand Catalysts for Some Asymmetric Reactions", Chemical Journal of Chinese Universities, vol. 22, No. 10, pp. 71-76, (2001), (with English abstract and partial English translation).
Davenport, Adam J. et al., "Chiral pyridine imidazolines from $C_1$-symmetric diamines: Synthesis, arene ruthenium complexes and application as asymmetric catalysis for Diels-Alder reactions", Journal of Organometallic Chemistry, vol. 691, No. 16, pp. 3445-3450, (2006).
Hatano, Manabu et al., "Highly Active Chiral Phosphoramide-Zn(II) Complexes as Conjugate Acid-Base Catalysts for Enantioselective Organozinc Addition to Ketones", Organic Letters, vol. 9, No. 22, pp. 4535-4538, (2007).
Dosa, Peter I. et al., "Catalytic Asymmetric Addition of $ZnPh_2$ to Ketones: Enantioselective Formation of Quaternary Stereocenters", J. Am. Chem. Soc., vol. 120, No. 2, pp. 445-446, (1998).
Garcia, Celina et al., "A Practical Catalytic Asymmetric Addition of Alkyl Groups to Ketones", J. Am. Chem. Soc., vol. 124, No. 37, pp. 10970-10971, (2002).
Garcia, Celina et al., "Highly Enantioselective Catalytic Phenylation of Ketones with a Constrained Geometry Titanium Catalyst", Organic Letters, vol. 5, No. 20, pp. 3641-3644, (2003).
Jeon, Sang-Jin et al., "A Green Chemistry Approach to a More Efficient Asymmetric Catalyst: Solvent-Free and Highly Concentrated Alkyl Addidtions to Ketones", J. Am. Chem. Soc., vol. 127, No. 47, pp. 16416-16425, (2005).
Jeon, Sang-Jin et al., "Catalytic Asymmetric Addition of Alkylzinc and Functionalized Alkylzinc Reagents to Ketones", J. Org. Chem., vol. 70, No. 2, pp. 448-455, (2005).

(Continued)

*Primary Examiner* — Janet Andres
*Assistant Examiner* — Timothy R Rozof
(74) *Attorney, Agent, or Firm* — Oblon, Spivak, McClelland, Maier & Neustadt, L.L.P.

(57) ABSTRACT

Disclosed is a method for highly efficiently obtaining an optically active alcohol from a carbonyl compound highly enantioselectively. Also disclosed is a ligand used in such a method. Specifically, an optically active alcohol is obtained by reacting a carbonyl compound and an organozinc compound by using a ligand (L) shown below.

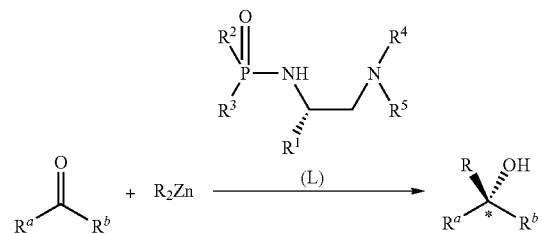

13 Claims, No Drawings

OTHER PUBLICATIONS

Cozzi, Pier Giorgio, "Enantioselective Alkynylation of Ketones Catalyzed by Zn(Salen) Complexes", Angew. Chem. Int. Ed., vol. 42, pp. 2895-2898, (2003).

Chinese Office Action issued Dec. 7, 2011 in patent application No. 200880008493.6 with English translation.

Andrei B. Ouryupin, et al., "Synthesis of N-Phosphorylated Aminoacids", Phosphorus, Sulfur, and Silicon, vol. 103, 1995, pp. 215-224.

Office Action issued Dec. 12, 2011, in European Patent Application No. 08720754.4-2117.

P. Savignac, et al.; "Synthesis de Diaminoethanes and Diaminopropanes"; Journal of Organometallic Chemistry, vol. 60, No. 1, Jan. 1, 1973, pp. 103-113, XP008113911.

A. A. Shtyrlina, et al.; "Reactions of Ethylenimides of Phosphorus Acids with n-Ethy-n-Propargylamine"; Journal of General Chemistry USSR; vol. 57; No. 5, Jan. 1, 1987, p. 1075, XP009153776.

Philip E. Sonnet, et al.; "Ring-Opening Reactions of P-1-Aziridinyl-N,N,N',N'-tetramethylphosphonic Diamides"; Journal of Organic Chemistry; vol. 31; No. 9; 1966; pp. 2962-2966; XP002664057.

Matthew J. Palmer, et al.; "The Use of Phosphinamide N-Protecting Groups in the Diastereoselective Reduction of Ketones"; Tetrahedron Letters; vol. 38; No. 13; Mar. 31, 1997; pp. 2315-2316; XP004056659.

Matthew J. Palmer, et al.; "The Use of Phophinamide N-Protecting Groups in the Diastereoselective Recuction of Ketones"; Tetrahedron; vol. 54, No. 30, Jul. 23, 1998; pp. 8827-8840; XP004124048.

Kangying Li, et al.; "Asymmetric carbonyl reduction with borane catalyzed by chiral phosphinamides derived from L-amino acid"; Tetrahedron Asymmetry; vol. 14; No. 1; Jan. 6, 2003; pp. 95-100 XP004404159.

Z-H Zhou et al.; "Synthesis of new chiral phosphorus compounds as ligand catalysts for some asymmetric reactions"; Chemical Journal of Chinese Universities; vol. 22, No. 10; Jan. 1, 2001; pp. 71-76; XP008115671.

Adam J. Davenport et al.; "Chiral pyridine imidazolines from $C_1$-symmetric diamines: Syntheis, arene ruthenium complexes and application as asymmetric catalysis for Diels-Alder reactions"; Journal of Organometallic Chemistry; vol. 691; No. 16; Aug. 1, 2006; pp. 3445-3450; XP005527957.

Jing Chen et al.; "A carbonyl oxygen migration in electrospray ionization mass spectrometry and its application in differentiating α- and β-alanyl peptides"; Journal of Mass Spectrometry; vol. 37; No. 9; Sep. 1, 2002; pp. 934-939; XP002664058.

Si-Oh Li et al.; Synthesis of N-Phosphorylated Derivatives of Amino Acids; Journal of the American Chemical Society; vol. 77, No. 7, 1955; pp. 1866-1870; XP002664059.

\* cited by examiner

PHOSPHORAMIDE COMPOUND, METHOD FOR PRODUCING THE SAME, LIGAND, COMPLEX, CATALYST AND METHOD FOR PRODUCING OPTICALLY ACTIVE ALCOHOL

TECHNICAL FIELD

The present invention relates to a novel phosphoramide compound and a method for producing the same. Additionally, the present invention relates to a ligand composed of the phosphoramide compound, a complex comprising the ligand, and a catalyst comprising the complex. Further, the present invention relates to a method for producing an optically active alcohol using the above-mentioned phosphoramide compound or the like.

DESCRIPTION OF THE RELATED ART

As an alcohol synthesis method, an alkyl addition reaction is known in which a carbonyl compound such as an aldehyde compound and a ketone compound is reacted with an organometal nucleophilic agent.

Many of biologically active substances are optically active substances having an asymmetric carbon atom. It is therefore important to obtain an optically active substance that has a desired absolute configuration. For example, optically active substances can be obtained in such a manner that a racemic mixture is synthesized, and then an optically active substance is isolated by optical resolution etc. However, this method requires a chemical alteration and thus is inefficient. For this reason, asymmetric synthesis methods by which optically active substances can be obtained selectively have long been under development. For example, the following methods are known as the method for obtaining optically active alcohols by reaction of a carbonyl compound with an organometal nucleophilic agent.

An asymmetric phenylation reaction for obtaining an optically active tertiary alcohol is disclosed in Non-Patent document 1. It is described that the enantiomeric excess (ee) of the product is 91% ee in Non-Patent document 1.

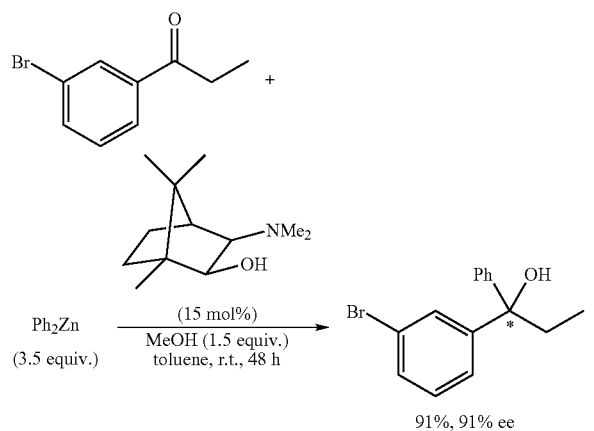

Methods for obtaining an optically active tertiary alcohol by adding a sulfonamide compound having a specific structure, and reacting a ketone with diethylzinc using Ti(Oi-Pr)$_4$ as a reactant are disclosed in Non-Patent Documents 2 to 5. One example thereof is as follows. Non-Patent Documents 2 to 5 disclose that the enantiomeric excess (ee) of the product is up to 99% ee.

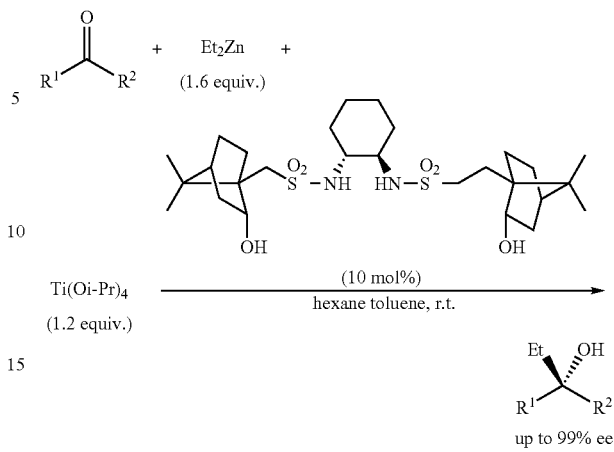

Non-Patent Document 6 discloses a method for obtaining an optically active tertiary alcohol by an asymmetric alkynylation reaction of aromatic and aliphatic ketones.

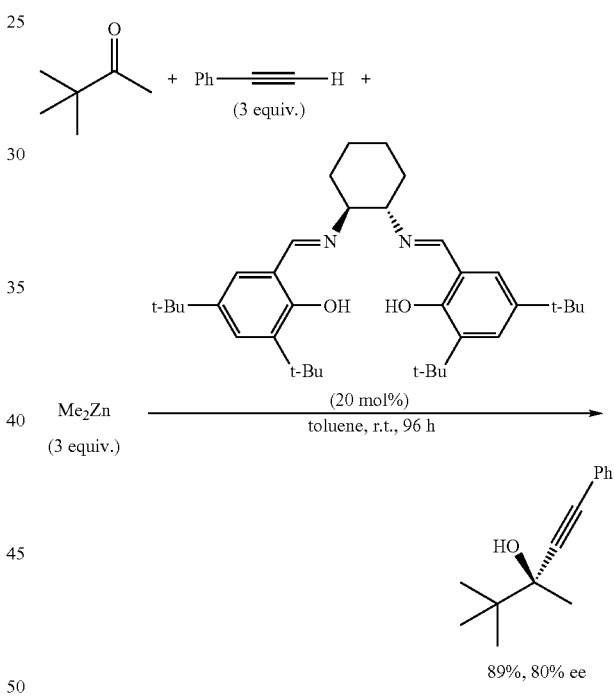

Additionally, a method for producing an optically active alcohol by adding a dialkylzinc to an aldehyde is disclosed in Patent Document 1. It is described that an asymmetric catalyst having a phosphine oxide unit or phosphine sulfide unit at the 3- and 3'-positions of the binaphthol skeleton is used in Patent Document 1.

[Non-Patent Document 1] J. Am. Chem. Soc., 1998, 120, 445-446
[Non-Patent Document 2] J. Am. Chem. Soc., 2002, 124, 10970-10971
[Non-Patent Document 3] J. Org. Lett., 2003, 5, 3641-3644
[Non-Patent Document 4] J. Am. Chem. Soc., 2005, 127, 16416-16425
[Non-Patent Document 5] J. Org. Chem., 2005, 70, 448-455
[Non-Patent Document 6] Angew. Chem. Int. Ed. 2003, 42, 2895-2898

[Patent Document 1] Japanese Patent Laid-Open Application Publication No. JP-A 2006-35125

DISCLOSURE OF THE INVENTION

Problems to be Solved by the Invention

An optically active alcohol is an important compound as a synthetic intermediate for drugs and the like. Hence, a method of synthesizing an optically active alcohol by an alkyl addition reaction in which a carbonyl compound is reacted with an organometal nucleophilic agent has been required.

Particularly, the synthesis of a tertiary alcohol is limited to alkyl addition reaction of a ketone using an organometal nucleophilic agent. Additionally, the alkyl addition reaction is accompanied by side reactions, as described below, such as a reduction reaction and an aldol reaction. It is thus difficult to obtain only the desired tertiary alcohol in sufficient yield. Moreover, the enantioselective production of an optically active tertiary alcohol using an asymmetric catalyst is considered extremely difficult.

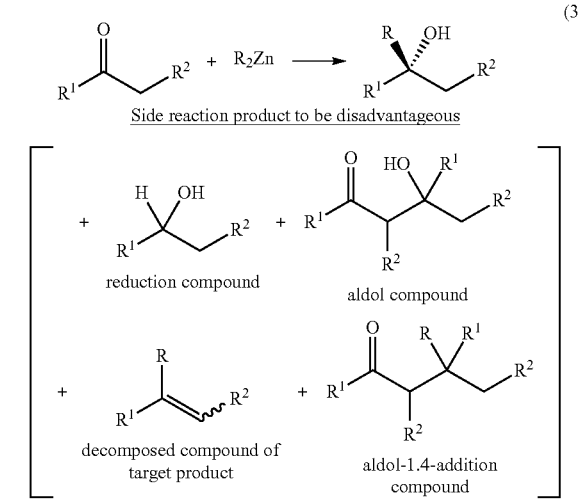

When viewed globally, only the research groups as described in Non-Patent Documents 1 to 6 have been successful in catalystic asymmetric synthesis of tertiary alcohols. However, these methods are inferior in practicality; the type of applicable alkylating agents is limited, and a large amount of titanium additive is required for the reaction.

An object of the present invention is to provide a method for obtaining an optically active alcohol using a carbonyl compound with a higher efficiency and higher enantioselectivity than before. Another object of the present invention is to provide a catalyst, a ligand and a novel phosphoramide compound constituting the ligand, that lead to an optically active alcohol with a higher efficiency and higher enantioselectivity than before, and a method for producing such a phosphoramide compound.

Means for Solving Problems

The phosphoramide compound of the present invention is characterized by being represented by the following general formula (1) or (1').

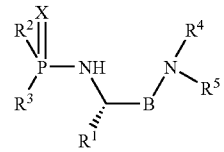

(1)

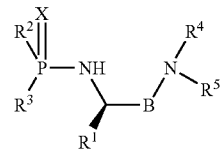

(1')

(In the formula, $R^1$ to $R^5$ are each independently monovalent hydrocarbon groups, $R^2$ and $R^3$ are each bound to a phosphorus atom directly or via an atom other than carbon atom, $R^2$ and $R^3$ may be bonded to each other to form a ring, and $R^4$ and $R^5$ may be bonded to each other to form a ring, X is an oxygen atom or sulfur atom, and B is a methylene group or carbonyl group.)

The method for producing the phosphoramide compound of the present invention is characterized by comprising the steps of:

(A) protecting the amino group of a compound represented by the following general formula (2a) or (2b) with a protective group to form a compound represented by the following general formula (3a) or (3b);

(B) reacting the compound represented by the general formula (3a) or (3b) with an amine compound to form an amide compound represented by the following general formula (4a) or (4b);

(C) deprotecting the protective group of the amine compound represented by the general formula (4a) or (4b), or deprotecting the protective group of the amine compound represented by the general formula (4a) or (4b) and reducing the amide group of the amide compound represented by the general formula (4a) or (4b), to form a compound represented by the following general formula (5a) or (5b); and (D) reacting the compound represented by the general formula (5a) or (5b) with a phosphorus compound represented by the following general formula (6) to form a phosphoramide compound of the present invention.

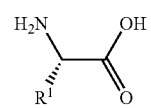

(2a)

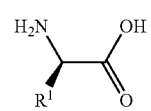

(2b)

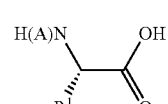

(3a)

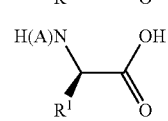

(3b)

(4a)
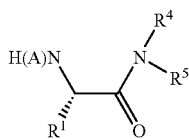

(4b)
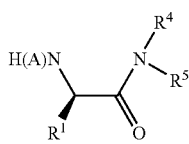

(5a)
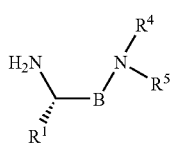

(5b)
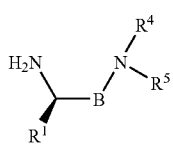

(6)
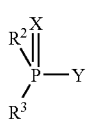

(In the formulae, $R^1$ to $R^5$ are each independently monovalent hydrocarbon groups, $R^2$ and $R^3$ are each bound to a phosphorus atom directly or via an atom other than carbon atom, $R^2$ and $R^3$ may be bound to each other to form a ring, $R^4$ and $R^5$ may also be bound to each other to form a ring, X is an oxygen atom or sulfur atom, Y is a halogen atom, A is a protective group, and B is a methylene group or carbonyl group.)

The ligand of the first embodiment according to the present invention is characterized in that it is the phosphoramide compound of the present invention. Additionally, the ligand of the second embodiment according to the present invention is characterized by represented by the following formula (8a), (8b), (9a) or (9b).

(8a)
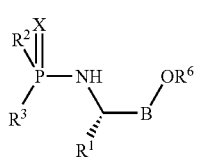

(8b)
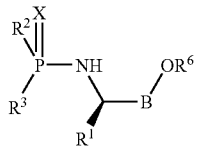

(9a)
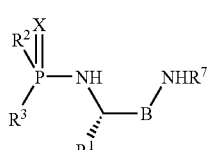

(9b)
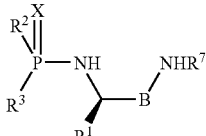

(In the formula, $R^1$ to $R^3$ and $R^7$ each independently monovalent hydrocarbon groups, $R^2$ and $R^3$ are each bound to a phosphorus atom directly or via an atom other than carbon atom, $R^6$ is a hydrogen atom or a monovalent hydrocarbon group, X is an oxygen atom or sulfur atom, and B is a methylene group or carbonyl group.)

The complex of the present invention is characterized in that a central metal is zinc atom, and a ligand is the ligand of the present invention. Additionally, the catalyst of the present invention is characterized by comprising the complex of the present invention.

The method for producing an optically active alcohol of the first embodiment according to the present invention is characterized in that the phosphoramide compound of the present invention or the ligand of the present invention is added to react a carbonyl compound with an organozinc compound represented by the following general formula (11) or with organozinc compounds represented by the following general formulae (12) and (13).

$$ZnR^{10}R^{11} \quad (11)$$

$$ZnR^{12}R^{13} \quad (12)$$

$$ZnR^{14}R^{15} \quad (13)$$

(In the formulae, $R^{10}$ and $R^{11}$ are each independently monovalent hydrocarbon groups, and at least one of them is an alkyl group, alkenyl group or alkynyl group, $R^{12}$ and $R^{13}$ are each independently aryl group, arylalkyl group or arylalkenyl group, and $R^{14}$ and $R^{15}$ are each independently alkyl group, alkenyl group or alkynyl group.)

The method for producing an optically active alcohol of the second embodiment according to the present invention is characterized in that a carbonyl compound is subjected to reaction with an organozinc compound represented by the following general formula (11) or with organozinc compounds represented by the following general formulae (12) and (13) in the presence of the complex of the present invention or the catalyst of the present invention.

$$ZnR^{10}R^{11} \quad (11)$$

$$ZnR^{12}R^{13} \quad (12)$$

$$ZnR^{14}R^{15} \quad (13)$$

(In the formulae, $R^{10}$ and $R^{11}$ are each independently monovalent hydrocarbon groups, and at least one of them is an alkyl group, alkenyl group or alkynyl group, $R^{12}$ and $R^{13}$ and are each independently aryl group, arylalkyl group or arylalkenyl group, and $R^{14}$ and $R^{15}$ are each independently alkyl group, alkenyl group or alkynyl group.)

Effects of the Invention

According to the present invention, an alkyl addition reaction in which a carbonyl compound such as an aldehyde and a ketone is reacted with an organometal nucleophilic agent can be performed using a novel phosphoramide compound as a ligand. As a result, an optically active alcohol can be synthesized with a higher efficiency and higher enantioselectivity than before. When the optically active alcohol synthesized by the present invention is used as a synthetic intermediate for drugs or pesticides (e.g., synthetic intermediates for clemastine that is often used as an antihistamine), the target drugs or pesticides can be produced with a high efficiency.

BEST MODE FOR CARRYING OUT THE INVENTION (1) Phosphoramide Compound and Method for Producing the Same The phosphoramide compound of the present invention is characterized by being represented by the above-described general formula (1) or (1').

In the general formulae (1) and (1'), $R^1$ to $R^5$ are each independently monovalent hydrocarbon groups. Examples of the monovalent hydrocarbon group include an alkyl group, an alkenyl group, an alkynyl group, an aryl group, an arylalkyl group and an arylalkenyl group.

The number of carbon atoms in the alkyl, alkenyl and alkynyl groups (hereinafter generically referred to as "alkyl group etc.") is not particularly limited. The number of carbon atoms in the above-mentioned alkyl group is usually 1 to 12, preferably 1 to 10, more preferably 1 to 8, further preferably 1 to 6, and particularly 1 to 4. Moreover, the number of carbon atoms in the above-mentioned alkenyl and alkynyl groups is usually 2 to 12, preferably 2 to 10, more preferably 2 to 8, further preferably 2 to 6, and particularly 2 to 4. When the alkyl group etc. have a cyclic structure, the number of carbon atoms in each of the alkyl group etc. is usually 4 to 12, preferably 4 to 10, more preferably 5 to 8, and further preferably 6 to 8.

The structure of the alkyl group etc. is not particularly limited. The alkyl group etc. may have a straight or branched chain structure. The alkyl group etc. may have a chain or cyclic structure (cycloalkyl, cycloalkenyl, and cycloalkynyl groups). Additionally, the alkyl group etc. may have one or more types of other substituents. Furthermore, the alkyl group etc. may contain one or more atoms other than carbon atom and hydrogen atom. For example, the alkyl group etc. may have, as a substituent, a substituent containing atoms other than carbon atom and hydrogen atom. Moreover, the alkyl group etc. may include one or more atoms other than carbon atom and hydrogen atom in the chain or cyclic structure. Example of the atom other than carbon atom and hydrogen atom include at least one of oxygen atom, nitrogen atom and sulfur atom.

Examples of the above-mentioned alkyl group include methyl group, ethyl group, n-propyl group, i-propyl group, n-butyl group, i-butyl group, sec-butyl group, t-butyl group, pentyl group, isopentyl group, neopentyl group, hexyl group, heptyl group, octyl group and 2-ethylhexyl group. Examples of the above-mentioned cycloalkyl group include cyclopentyl group, cyclohexyl group, cycloheptyl group and 2-methylcyclohexyl group. Examples of the above-mentioned alkenyl group include vinyl group, allyl group and isopropenyl group. Examples of the above-mentioned cycloalkenyl group include cyclohexenyl group.

The number of carbon atoms in the aryl, arylalkyl and arylalkenyl groups (hereinafter generically referred to as "aryl group etc.") is not particularly limited. The number of the aryl group etc. is usually 6 to 15, preferably 6 to 12, and more preferably 6 to 10.

The structure of the aryl group etc. is not particularly limited. The aryl group etc. may have one or more types of other substituents. For example, the aromatic ring contained in the aryl group etc. may have one or more types of other substituents. The position of the substituent may be any of o-, m-, and p-positions. Specific examples of the substituent include at least one of a halogen atom, an alkyl group, an alkenyl group, a nitro group, an amino group, a hydroxy group and an alkoxy group. When the substituent is located on the aromatic ring, the position of the substituent may be any of o-, m-, and p-positions.

The above-mentioned halogen atom may be at least one of a fluorine atom, a chlorine atom and a bromine atom.

Examples of the above-mentioned alkyl and alkenyl groups include at least one of an alkyl group and an alkenyl group, having 1 to 6 carbon atoms, and preferably 1 to 4 carbon atoms. Specific examples of the above-mentioned alkyl and alkenyl groups include at least one of methyl group, ethyl group, n-propyl group, i-propyl group, i-butyl group, sec-butyl group and t-butyl group. In addition, the above-mentioned alkyl and alkenyl groups may further have other substituents, and may be a halogenated alkyl and halogenated alkenyl groups. For example, the alkyl group may be exemplified as a group in which a part or all of hydrogen atoms in methyl or ethyl group are substituted with a halogen atom (at least one of a fluorine atom, a chlorine atom and a bromine atom) such as $CF_3-$, $CCl_3-$ or the like.

Examples of the above-mentioned alkoxy group include an alkoxy group having 1 to 6 carbon atoms, preferably 1 to 4 carbon atoms, and more preferably 1 to 3 carbon atoms. Specific examples of the above-mentioned alkoxy group include methoxy group, ethoxy group, n-propoxy group, i-propoxy group, n-butoxy group, i-butoxy group, sec-butoxy group and t-butoxy group.

The aromatic ring contained in the aryl group etc. may have one or more types of a hetero atom such as oxygen atom, nitrogen atom, and sulfur atom. That is, the aromatic ring contained in the aryl group etc. may be an aromatic heterocycle (furan, thiophene, pyrrole, benzofuran, indole, thiophene, pyrazole, imidazole, triazole, isoxazole, oxazole, isothiazole, thiazole, pyridine, quinoline, isoquinoline, pyrimidine, and the like).

Specific examples of the above-mentioned aryl group include phenyl group, tolyl group, ethylphenyl group, xylyl group, cumenyl group, mesityl group, methoxyphenyl group (o-, m-, and p-), ethoxyphenyl group (o-, m-, and p-), 1-naphthyl group, 2-naphthyl group, biphenylyl group and the like. Specific examples of the above-mentioned arylalkyl group include benzyl group, methoxybenzyl group (o-, m-, and p-), ethoxybenzyl group (o-, m-, and p-), and phenethyl group. Specific examples of the above-mentioned arylalkenyl group include styryl group and cinnamyl group.

$R^2$ and $R^3$ are each directly bound to a phosphorus atom or are bound to the phosphorus atom via an atom other than carbon atom (hereinafter this binding is referred to as "indirect binding"). Examples of the atom other than carbon atom include an oxygen atom, a nitrogen atom and a sulfur atom. Specific examples of the indirect binding include a structure "$R^2$ (or $R^3$)—O—P" and a structure "$R^2$ (or $R^3$)—N(E)-P". Of course, both $R^2$ and $R^3$ may be bound to the phosphorus atom directly or indirectly, or one of $R^2$ and $R^3$ may be directly bound to the phosphorus atom, and the other may be indirectly bound to the phosphorus atom. When $R^2$ and $R^3$ are bound to the phosphorus atom indirectly (e.g., via an oxygen atom), specific $R^2$ and $R^3$ can each independently be monovalent hydrocarbon groups having 3 or more carbon atoms, preferably 4 or more carbon atoms, and more preferably 4 to 10 carbon atoms.

When the atom other than carbon atom is a nitrogen atom, E bound to the nitrogen atom may be a hydrogen atom or other monovalent hydrocarbon group. The other monovalent hydrocarbon group may be the same as or different from $R^2$ (or $R^3$). Further, $R^2$ (or $R^3$) and the other monovalent hydrocarbon group may be bound to each other to form a ring. The explanation of $R^1$ to $R^3$ of the phosphoramide compound of the present invention is applicable to the structure and contents of the other monovalent hydrocarbon group. When two monovalent hydrocarbon groups are bonded to the above nitrogen atom in the present invention, at least one of them may correspond to $R^2$ (or $R^3$). Examples of the other monovalent hydrocarbon group include an alkyl group, alkenyl group and alkynyl group, having 1 to 5 carbon atoms. Specific examples of the other monovalent hydrocarbon group include methyl group, ethyl group, n-propyl group and i-propyl group. Specific examples of the above-mentioned structure "$R^2$ (or $R^3$)—N(E)-P" include a structure "$(CH_3)_2N$—P-" and a structure "$(CH_3CH_2)_2N$—P—".

$R^2$ and $R^3$ may be bound to each other to form a ring. $R^4$ and $R^5$ may also be bound to each other to form a ring. When $R^2$ and $R^3$ are bound to each other to form a ring, and $R^4$ and $R^5$ are bound to each other to form a ring, the structure of such rings is not particularly limited. For example, the number of ring members is not particularly limited. When $R^2$ and $R^3$ are bound to each other to form a ring, the number of ring members may be four to ten, and preferably five to eight, including the phosphorus atom to which $R^2$ and $R^3$ are bound. When $R^4$ and $R^5$ are bound to each other to form a ring, the number of ring members may be four to ten, and preferably five to eight, including the nitrogen atom to which $R^4$ and $R^5$ are bound. The ring may contain a hetero atom such as an oxygen atom, a nitrogen atom and a sulfur atom in its structure. In addition, the ring may have other substituent. Further, the ring may have an unsaturated bond in its structure.

Specific examples of the ring formed by binding of $R^2$ and $R^3$ are shown below.

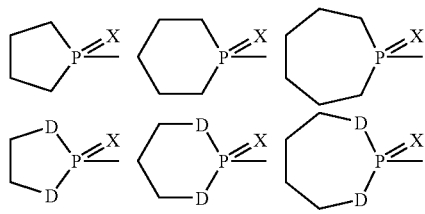

(In the above formulae, D is a hetero atom such as an oxygen atom, a nitrogen atom and a sulfur atom.)

Specific examples of the ring formed by binding of $R^4$ and $R^5$ are shown below. Specific examples of the ring include a five-membered ring structure formed by tetramethylene group, a six-membered ring structure formed by pentamethylene group, a seven-membered ring structure formed by hexamethylene group, and a eight-membered ring structure formed by heptamethylene group. In addition, examples of the structure containing a hetero atom in the ring structure include a structure containing an oxygen atom (a morpholyl group).

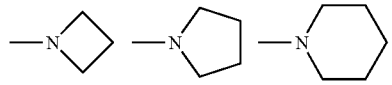

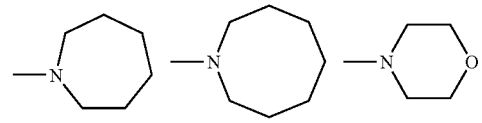

$R^1$ to $R^5$ may be all the same groups or may be partly or completely different groups. For example, $R^2$ may be the same as or different from $R^3$. Additionally, $R^1$ to $R^3$ may be all the same groups. Among $R^1$ to $R^3$, $R^2$ and $R^3$ may be the same groups, and $R^1$ may be different from these groups. $R^4$ may be the same as or different from $R^5$.

Specific structures of $R^1$ to $R^5$ are not particularly limited. As the structures of $R^1$ to $R^5$, each structure described above can be adopted in a suitable combination, if necessary.

$R^1$ may be an alkyl group, an arylalkyl group or an arylalkenyl group. The alkyl group may be an alkyl group explained above, particularly methyl group, ethyl group, n-propyl group, i-propyl group, n-butyl group, sec-butyl group or t-butyl group. The arylalkyl group may be an arylalkyl group explained above, particularly benzyl group, or o-, m-, and p-alkoxybenzyl groups such as methoxybenzyl group and ethoxybenzyl group. In addition, $R^1$ can be an alkyl group, an aryl group, an arylalkyl group or an arylalkenyl group and be one which is different from either or both of $R^2$ and $R^3$. When $R^2$ and $R^3$ are the above-mentioned alkyl groups etc. (for example, an alkyl group having 5 or more carbon atoms, 3 or less carbon atoms, or 2 or less carbon atoms), $R^1$ can be an aryl group, an arylalkyl group or an arylalkenyl group.

$R^2$ and $R^3$ may be same or different cycloalkyl group, aryl group, arylalkyl group or arylalkenyl group. The aryl group may be an aryl group explained above, particularly phenyl group, 1-naphthyl group, 2-naphthyl group, o-, m- and p-alkoxyphenyl groups such as methoxyphenyl group and ethoxyphenyl group, or an o-, m- and p-halogenated alkylphenyl group such as trifluoromethylphenyl group and trichloromethylphenyl group. The arylalkyl group may be an arylalkyl group explained above, particularly benzyl group, or o-, m-, and p-alkoxybenzyl groups such as methoxybenzyl group and ethoxybenzyl group. In addition, when $R^1$ is the above-mentioned alkyl groups etc., at least one of $R^2$ and $R^3$ may be a cycloalkyl group, an aryl group, an arylalkyl group or an arylalkenyl group.

In the general formula (1) or (1') described above, X is an oxygen atom or sulfur atom. X is usually an oxygen atom.

Examples of the phosphoramide compound of the present invention include compounds represented by the following general formulae.

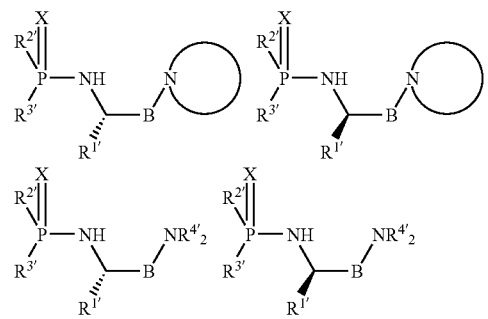

In the above formulae, X is an oxygen atom or sulfur atom. B is a methylene group or carbonyl group. $R^{1''}$ is an alkyl group or arylalkyl group having 2 or more carbon atoms, preferably 3 or more carbon atoms, and more preferably 3 to 10 carbon atoms, which is different from $R^{2'}$ and $R^{3'}$. $R^{2'}$ and $R^{3'}$ are same or different cycloalkyl group, aryl group, arylalkyl group or aryl alkenyl group. $R^{4'}$ is an alkyl group, alkenyl group or alkynyl group. The explanation of $R^1$ to $R^4$ is applicable to $R^{1'}$ to $R^{4'}$.

Specific examples of the phosphoramide compound of the present invention include the following compounds. The configuration of the group corresponding to $R^1$ may be reversed in these compounds. "Cy" in the following formula is a cycloalkyl group (a cyclohexyl group and the like).

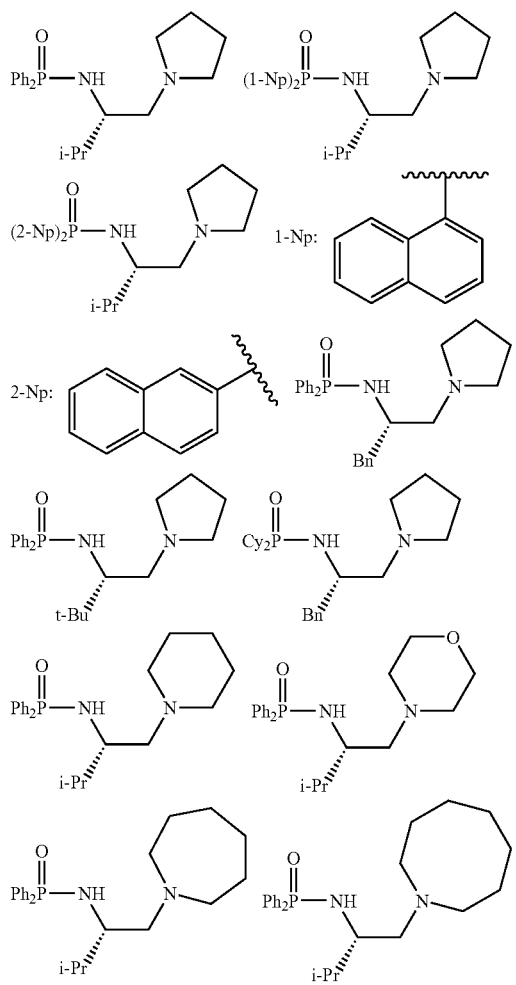

The method for producing the phosphoramide compound of the present invention is not particularly limited. The phosphoramide compound of the present invention can be produced by the method for producing the phosphoramide compound of the present invention.

(2) Method for Producing Phosphoramide Compound

The method for producing the phosphoramide compound of the present invention comprises Steps (A) to (D), as described above. In the method for producing the phosphoramide compound of the present invention, the explanation of $R^1$ to $R^5$ and X in the phosphoramide compound of the present invention is applicable.

<Step (A)>

The step (A) is a step to protect the amino group of the compound represented by the general formula (2a) or (2b) described above (hereinafter referred to as "compound (2a) or (2b)"), with a protective group to form the compound represented by the general formula (3a) or (3b) described above (hereinafter referred to as "compound (3a) or (3b)").

Commercially available amino acids (natural and non-natural amino acids) can be used as the compound (2a) or (2b), which is a starting material. Of course, the compound (2a) and (2b) may be ones synthesized by any method. Additionally, the starting material may consist only of an optically active substance of the compound (2a) or (2b), or may be a mixture of an optically active substance such as a racemic modification. When the starting material is a mixture of an optically active substance such as racemic modification, an optically active phosphoramide compound can be obtained by optical resolution after the reaction. The process for the optical resolution is not particularly limited, and known processes are applicable. In the production method of the present invention, the optically active substances of the compound (2a) and (2b) are preferably used as the starting material because an optically active phosphoramide compound can be obtained without an optical resolution.

A in the above formula is a protective group. The structure of the protective group is not particularly limited so long as it can protect the amino group contained in the compound (2a) or (2b). Examples of the protective group include t-butoxycarbonyl group (Boc), benzyloxycarbonyl group, and t-amyloxycarbonyl group. For example, the above-described t-butoxycarbonyl group, which is a protective group, can be introduced into the amino group by reaction of the compound (2a) or (2b) with di-t-butyl carbonate.

The reaction conditions for the step (A) are also not particularly limited. The step (A) can be carried out by reacting, in a solvent such as ethanol, the compound (2a) or (2b) with a protecting reagent for introducing the above-mentioned protective group. The reaction is preferably carried out at room temperature (20° C.-30° C.), although the reaction temperature is not particularly limited.

<Step (B)>

The step (B) is a step to react the compound (3a) or (3b) with an amine compound to form the amide compound represented by the general formula (4a) or (4b) described above (hereinafter referred to as "amide compound (4a) or (4b)").

In the step (B), the type of the amine compound is not particularly limited so long as the amide compound (4a) or (4b) can be obtained. A secondary amine having $R^4$ and $R^5$ is usually used. In the step (B), an amide compound may be obtained using a primary amine having $R^4$ (or $R^5$), and then $R^5$ (or $R^4$) may be introduced by N-alkylation reaction, thereby forming the amide compound (4a) or (4b). In addition, the amine compound may be a cyclic amine compound or an acyclic amine compound. An amine compound having four to ten-membered ring and preferably five to eight-membered ring can be used as the cyclic amine compound. The ring may contain a hetero atom such as an oxygen atom, a nitrogen atom and a sulfur atom in its structure. Further, the ring may have other substituents. Moreover, the ring may have an unsaturated bond in its structure. Specific examples of the cyclic amine compound include pyrrolidine, piperidine and morpholine.

The reaction conditions for the step (B) are not particularly limited so long as the amide compound (4a) or (4b) can be obtained. An alkyl halide such as dichloromethylene can be used as a solvent. The reaction is preferably performed at room temperature (20° C.-30° C.), although the reaction temperature is not particularly limited. The reaction time is usually in the range from 1 to 48 hours, preferably from 3 to 30 hours, and more preferably from 12 to 24 hours. Additionally, dicyclocarbodiimide (DCC), 1-hydroxybenzotriazole (HOBt) and the like can be added.

Further, the proportions of the compound (3a) or (3b) and the amine compound are not also particularly limited in the producing method of the present invention. Generally, 1 to 3 equivalents, and preferably 1.5 to 2.5 equivalents of the amine compound can be used per equivalent of the compound (3a) or (3b). Moreover, the proportions of DCC and other components are not also particularly limited in the producing method of the present invention. For example, 1 to 2 equivalents of each of DCC and HOBt can be used per equivalent of the compound (3a) or (3b) in the producing method of the present invention.

<Step (C)>

The step (C) is a step to deprotect the protective group of the amide compound (4a) or (4b) (hereinafter referred to as "step (C1)"), or deprotect the protective group of the amide compound (4a) or (4b) while reducing the amide group of the amide compound (4a) or (4b) (hereinafter referred to as "step (C2)"), to form the compound represented by the general formula (5a) or (5b) described above (hereinafter referred to as "compound (5a) or (5b)").

In the present invention, a compound wherein B is a carbonyl group can be formed by the step (C1). Additionally, a compound wherein B is a methylene group can be formed by the step (C2) in the present invention.

The deprotection method and its reaction conditions are not particularly limited in the step (C). The deprotection method and its reaction conditions can be suitably selected according to the type of the protective group. When the protective group is, for example, a t-butoxycarbonyl group, the protective group can be deprotected by an acid treatment using AcOH, AcCl, HBr or the like.

The method for the reduction of the amide group and its reaction conditions are not particularly limited in the step (C). Example of the method for the reduction of the amide group includes a method in which an amide group is reduced with lithium aluminum hydride ($LiAlH_4$) in a solvent of tetrahydrofuran or ether. In this case, the amount of $LiAlH_4$ is usually in the range from 1 to 10 equivalents, preferably from 2 to 8 equivalents, and more preferably from 3 to 7 equivalents.

In the step (C2), the order of the "reduction of the amide group" and "deprotection of the protective group" is not particularly limited. The "deprotection of the protective group" may be performed after performing the "reduction of the amide group" in the present invention. Alternatively, the "reduction of the amide group" can be performed after performing the "deprotection of the protective group" in the present invention.

<Step (D)>

The step (D) is a step in which the compound (5a) or (5b) is reacted with the phosphorus compound represented by the formula (6) described above (hereinafter referred to as "phosphorus compound (6)") to form a phosphoramide compound of the present invention.

The explanation of $R^2$, $R^3$ and X in the phosphoramide compound of the present invention is applicable to $R^2$, $R^3$ and X in the above formula (6). Moreover, Y in the formula (6) is a halogen atom. Examples of the halogen atom include fluorine atom, chlorine atom and bromine atom.

The amount of the phosphorus compound (6) to be used is not particularly limited in the step (D). The amount of the phosphorus compound (6) is usually in the range from 1 to 3 equivalents, preferably from 1 to 2 equivalents, and more preferably from 1 to 1.5 equivalents based on 1 equivalent of the compound (5a) or (5b).

An amine compound can further be coexistent in the step (D). Coexistence of the amine compound can improve the reaction efficiency of the compound (5a) or (5b) with the phosphorus compounds (6). Examples of the amine compound include triethyl amine and the like. The amount of the amine compound is usually in the range from 1 to 4 equivalents, preferably from 1 to 3 equivalents, and more preferably from 1 to 2.5 equivalents per equivalent of the compound (5a) or (5b).

The reaction conditions of the step (D) are not particularly limited. The reaction temperature may be room temperature (20° C.-30° C.). The reaction time may be in the range from 1 to 24 hours, and is preferably from 1 to 12 hours, more preferably from 1 to 6 hours.

<Others>

The phosphoramide compound of the present invention represented by the above formula (1) or (1') wherein X is an oxygen atom can be obtained by reaction with a halogenated phosphine oxide having $R^2$ and $R^3$. Further, the phosphoramide compound of the present invention represented by the above formula (1) or (1') wherein X is a sulfur atom can be obtained by reaction with a halogenated phosphine sulfide having $R^2$ and $R^3$.

Each step in the production method of the present invention may be carried out after isolation of each product, or may be carried out in a series without isolation of the product.

The production method of the present invention may include steps other than the above-described steps. For example, the other steps are exemplified as other chemical reaction steps. In addition, the production method of the present invention may optionally comprise, as other steps, optical resolution step for separating only optically active substances, and physical operation steps including concentration, purification, isolation and the like of the product.

(3) Ligand

The ligand of the first embodiment of the present invention is expressed by the phosphoramide compound of the present invention. In addition, the ligand of the second embodiment of the present invention is expressed by the formula (8a), (8b), (9a) or (9b), described above. The explanation of $R^1$ to $R^3$ and X of the phosphoramide compound of the present invention is applicable to $R^1$ to $R^3$ and X in the ligand of the second embodiment of the present invention.

In the ligand of the second embodiment of the present invention, $R^6$ is a hydrogen atom or a monovalent hydrocarbon group, and $R^7$ is a monovalent hydrocarbon group. Examples of the monovalent hydrocarbon group include an alkyl group, an alkenyl group, an alkynyl group, an aryl group, an arylalkyl group and an arylalkenyl group. The explanation of $R^1$ to $R^3$ in the phosphoramide compound of the present invention is applicable to the type and structure of the monovalent hydrocarbon group. B is a methylene group or carbonyl group.

Specific structures of $R^1$ to $R^3$, and $R^6$ are not particularly limited. As the structures of $R^1$ to $R^3$, $R^6$, and $R^7$, for example, each structure illustrated above can be adopted in a suitable combination, if necessary. $R^6$ and $R^7$ may be the same as or different from $R^1$ to $R^3$.

Examples of the compounds represented by Formulae (8a), (8b), (9a) and (9b) include those having the following structures.

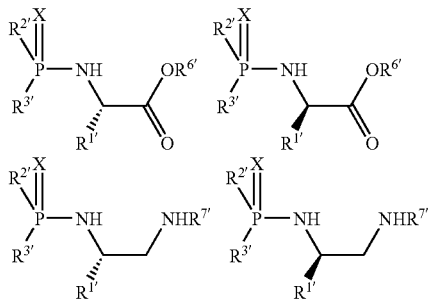

In the above formulae, X is an oxygen atom or sulfur atom. $R^{1'}$ is an alkyl group, aryl group or arylalkyl group, having two or more carbon atoms, preferably three of more carbon atoms, more preferably 3 to 10 which group is different from $R^{2'}$ and $R^{3'}$. $R^{2'}$ and $R^{3'}$ are same or different cycloalkyl group, aryl group, arylalkyl group or arylalkenyl group. $R^{6'}$ is an alkyl group (preferably an alkyl group having 1 to 5 carbon atoms) or arylalkyl group. $R^{7'}$ is an aryl group, arylalkyl group or arylalkenyl group. The explanation of $R^1$ to $R^3$ is applicable to $R^{1'}$ to $R^{3'}$. The explanation of $R^6$ and $R^7$ is applicable to $R^{6'}$ and $R^{7'}$.

(4) Complex

The complex of the present invention comprises zinc as the central metal, and the ligand of the present invention as the ligand.

The structure of the complex of the present invention is not particularly limited so long as the central metal is zinc and the ligand is that of the present invention. Specific example of the complex of the present invention includes a complex in which an organozinc compound represented by the general formula: $ZnR^8R^9$ is coordinated to the ligand of the present invention. Examples of the complex of the present invention include a complex represented by the following general formula (10).

$$L_m ZnR^8(ZnR^8R^9)_n \qquad (10)$$

$R^8$ and $R^9$ are each independently monovalent hydrocarbon groups. Examples of the monovalent hydrocarbon group include an alkyl group, an alkenyl group, an alkynyl group, an aryl group, an arylalkyl group and an arylalkenyl group. The explanation of $R^1$ to $R^3$ in the phosphoramide compound of the present invention is applicable to the type and structure of the monovalent hydrocarbon groups. $R^8$ may be the same as or different from $R^9$.

L is a ligand of the present invention or a compound obtained from the ligand in which the hydrogen atom on the nitrogen atom is eliminated. That is, the complex of the present invention may have a structure in which zinc is coordinated to the ligand of the present invention. Alternatively, the complex of the present invention may have a structure in which the hydrogen atom on the nitrogen atom is eliminated from the ligand of the present invention, and zinc is coordinated thereto (see the following formula). When an organozinc compound is added to the ligand of the present invention, gas generation may be observed. This is presumably because the complex (C) of the present invention is formed according to the following formula (note that this explanation is the inventor's presumption; therefore, this explanation and the following formulae are not intended to limit the scope of the present invention).

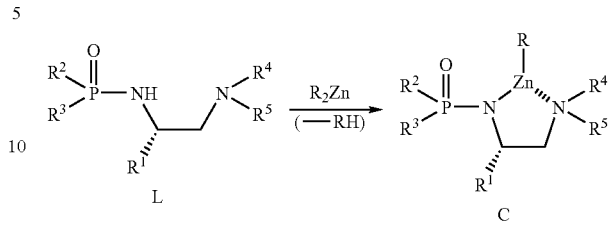

In the above formula, m is an integer in the range from 1 to 10, preferably from 1 to 8, more preferably from 1 to 5, further preferably form 1 to 3, and particularly from 1 to 2. In addition, n is an integer in the range from 0 to 10, preferably from 0 to 8, more preferably from 0 to 5, further preferably from 0 to 3, and particularly from 0 to 2. Usually, n is 1 or 0.

The complex of the present invention can be obtained by, for example, mixing the ligand of the present invention and an organozinc compound such as the organozinc compound represented by $ZnR^8R^9$ wherein $R^8$ and $R^9$ are each independently monovalent hydrocarbon groups, in a solvent such as an aliphatic hydrocarbon including hexane, heptane and the like, an aromatic hydrocarbon including toluene and the like, a halogenated alkyl compound including methylene chloride. Additionally, an alkyne can be mixed. In this case, it is considered that an alkynyl zinc obtained by reaction of the added organozinc compound with the alkyne is coordinated to the ligand of the present invention to form the complex of the present invention (note that this explanation is inventor's presumption; this explanation is not intended to limit the scope of the present invention). That is, the organic group contained in the added organozinc compound may be the same as or different from the organic group bonded to zinc atom that forms the complex of the present invention, for the complex of the present invention.

The form of the complex of the present invention is not particularly limited. The complex of the present invention may be present in a solvent, or may be present as a residue after the solvent is distilled off. Further, the complex of the present invention may be used as-prepared. Moreover, the complex of the invention may be, for example, formed in a reaction solvent without being isolated as a complex, and may be continuously used in the reaction.

(5) Catalyst

The catalyst of the present invention comprises the complex of the present invention.

The composition of the catalyst of the present invention is not particularly limited so long as the catalyst contains the complex of the present invention. The catalyst of the present invention may comprise components other than the complex of the invention. The form of the catalyst of the present invention is not particularly limited. The catalyst of the present invention may be present in a solvent, or may be present as a residue after the solvent is distilled off. Further, the catalyst of the invention may be used as-prepared. Moreover, the catalyst of the invention may be, for example, formed in a reaction solvent without being isolated as a catalyst, and may be continuously used in the reaction.

The catalyst can catalyze alkyl addition reaction in which a carbonyl compound such as an aldehyde and a ketone is reacted with an organometal nucleophilic agent. The catalyst can therefore be used as a catalyst for alcohol synthesis. Moreover, the catalyst exhibits excellent enantioselectivity.

The catalyst can therefore be used as a catalyst for the synthesis of an optically active alcohol. In particular, the catalyst can be used as a catalyst for the synthesis of an optically active tertiary alcohol by an alkyl addition reaction of a ketone, which is conventionally difficult to synthesize.

(6) Method for Producing Optically Active Alcohol

The method for producing optically active alcohol of the first embodiment according to the present invention is characterized in that the phosphoramide compound of the present invention or the ligand of the present invention is added, and a carbonyl compound such as an aldehyde compound and a ketone is reacted with an organozinc compound represented by the general formula (11) or with an organozinc compound represented by the general formulae (12) and (13).

The method for producing optically active alcohol of the second embodiment according to the present invention is characterized in that a carbonyl compound such as an aldehyde compound and a ketone is reacted with an organozinc compound represented by the general formula (11) or with an organozinc compound represented by the general formulae (12) and (13) in the presence of the complex of the present invention or the catalyst of the present invention.

There are differences between ketone and aldehyde when each of them is used in an alcohol synthesis using an organozinc compound. The differences are as follows. First, a ketone has a lower reactivity rather than an aldehyde due to three-dimensional and electronic factors. Secondary, the alcohol synthesis reaction itself is often difficult to advance due to low reactivity of an organozinc compound, and the reaction is sometimes accompanied by side reactions. Third, the enantioface discrimination of a ketone by a chiral catalyst is usually more difficult than the enantioface discrimination of an aldehyde. The conventional asymmetric alkyl addition reaction using a catalyst was therefore limited to the synthesis of an optically active secondary alcohol using an aldehyde. However, the method for producing an optically active alcohol of the present invention can be applied to the production of an optically active tertiary alcohol using a ketone compound, as well as the synthesis of an optically active secondary alcohol using an aldehyde compound. In particular, according to the alkyl addition reaction of a ketone in the present invention, an enantioselective optically active tertiary alcohol, which is conventionally difficult to synthesize, can be synthesized with a higher efficiency and high enantioselectivity than before. In the following, "optically active alcohol" refers to "optically active tertiary alcohol" when the starting material is a ketone compound, and when the starting material is an aldehyde compound, it refers to "optically active secondary alcohol".

The type and structure of the above-mentioned carbonyl compound, which is a starting material, are not particularly limited. The ketone compound may be an aromatic ketone or an aliphatic ketone. In addition, the aldehyde compound may be an aromatic aldehyde or an aliphatic aldehyde.

Examples of the ketone compound include ketone compounds represented by the general formula (14) and (15).

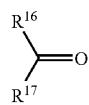

(14)

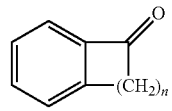

(15)

In the formula, $R^{16}$ is a monovalent hydrocarbon group having three or more carbon atoms. $R^{17}$ is a different monovalent hydrocarbon group from $R^{16}$. Examples of the monovalent hydrocarbon group include an alkyl group, an alkenyl group, an alkynyl group, an aryl group, an arylalkyl group and an arylalkenyl group. The explanation of $R^1$ to $R^3$ in the phosphoramide compound of the present invention is applicable to the types and structures of the alkyl group, alkenyl group, alkynyl group, aryl group, arylalkyl group and arylalkenyl group. $R^{17}$ in the general formula (14) can be a methyl group or an ethyl group.

In the general formula (15), n is an integer of 2 or more, preferably 2 to 6, and more preferably 2 to 5.

The aromatic ring in the general formula (15) may have one or more substituents. The position of the substituent may be o-, m- or p-positions. Examples of the substituent include at least one of a halogen atom, an alkyl group, an alkenyl group, a nitro group, an amino group, a hydroxy group and an alkoxy group. When a substituent is located on the aromatic ring, the position of the substituent may be o-, m- or p-positions.

The above-mentioned halogen atom may be at least one of a fluorine atom, a chlorine atom and a bromine atom.

Examples of the above-mentioned alkyl and alkenyl groups include at least one of alkyl group or alkenyl group having 1 to 6 carbon atoms, preferably 1 to 4 carbon atoms. Specific examples of the above-mentioned alkyl and alkenyl groups include at least one of methyl group, ethyl group, n-propyl group, i-propyl group, i-butyl group, sec-butyl group and t-butyl group. In addition, the above-mentioned alkyl and alkenyl groups may further have other substituents, and may be a halogenated alkyl and halogenated alkenyl groups. For example, the alkyl group may be exemplified as a group in which a part or all of hydrogen atoms in methyl or ethyl group are substituted with a halogen atom (at least one of a fluorine atom, a chlorine atom and a bromine atom) such as $CF_3—$, $CCl_3—$.

Examples of the above-mentioned alkoxy group include an alkoxy group having 1 to 6 carbon atoms, preferably 1 to 4 carbon atoms, and more preferably 1 to 3 carbon atoms. Specific examples of the above-mentioned alkoxy group include methoxy group, ethoxy group, n-propoxy group, i-propoxy group, n-butoxy group, i-butoxy group, sec-butoxy group and t-butoxy group.

Examples of the above-mentioned aldehyde compound include an aldehyde compound represented by the general formula: $R^{18}CHO$. In the formula, $R^{18}$ is a monovalent hydrocarbon group. Examples of the monovalent hydrocarbon group include an alkyl group, an alkenyl group, an alkynyl group, an aryl group, an arylalkyl group and an arylalkenyl group. The explanation of $R^1$ to $R^3$ in the phosphoramide compound of the present invention is applicable to the types and structures of the above-mentioned alkyl group, alkenyl group, alkynyl group, aryl group, arylalkyl group and arylalkenyl group.

In the general formula (11) described above, $R^{10}$ and $R^{11}$ are each independently monovalent hydrocarbon groups. Examples of the monovalent hydrocarbon group include an alkyl group, an alkenyl group, an alkynyl group, an aryl group, an arylalkyl group and an arylalkenyl group. The explanation of $R^1$ to $R^3$ in the phosphoramide compound of the present invention is applicable to the types and structures of the above-mentioned monovalent hydrocarbon group, alkyl group, alkenyl group and alkynyl group. $R^{10}$ may be the same as or different from $R^{11}$. In the general formula (11) described above, $R^{10}$ and $R^{11}$ can be each independently monovalent hydrocarbon groups, and at least one of them can be an alkyl, alkenyl or alkynyl group.

In the general formula (12) described above, $R^{12}$ and $R^{13}$ are each independently aryl group, arylalkyl group or arylalkenyl group. Additionally, in the general formula (13) described above, $R^{14}$ and $R^{15}$ are each independently alkyl group, alkenyl group or alkynyl group. The explanation of $R^1$ to $R^3$ in the phosphoramide compound of the present invention is applicable to the types and structures of the above-mentioned alkyl group, alkenyl group, alkynyl group, aryl group, arylalkyl group and arylalkenyl group. Additionally, $R^{12}$ may be the same as or different from $R^{13}$. $R^{14}$ may be the same as or different from $R^{15}$.

The amount and proportion of each component to be used are not particularly limited in the method for producing an optically active alcohol of the present invention. For example, the amount of the organozinc compound represented by the general formula (11) can usually be in the range from 1 to 5 equivalents, preferably 1 to 4 equivalents, and more preferably 1 to 3 equivalents, based on the above-mentioned carbonyl compound such as a ketone compound and an aldehyde compound. Similarly, the amount of the organozinc compound represented by the general formula (12) can usually be in the range from 1 to 3 equivalents, preferably 1 to 2 equivalents, and more preferably 1 to 1.5 equivalents. In addition, the amount of the organozinc compound represented by the general formula (13) can usually be in the range from 1 to 4 equivalents, preferably 1 to 3 equivalents, and more preferably 1 to 2.5 equivalents. Further, the equivalent ratio of the organozinc compound represented by the general formula (12) to the organozinc compound represented by the general formula (13) can usually be 1:(1 to 5), preferably 1:(1 to 4), more preferably 1:(1 to 3), and further preferably 1: (1 to 2).

Further, the amount of the phosphoramide compound of the present invention to be added can be usually in the range from 0.1% to 20% by mol, preferably from 0.5% to 15% by mol, more preferably from 1% to 15% by mol, and further preferably from 5% to 15% by mol based on the above-mentioned carbonyl compound such as ketone compound and aldehyde compound in the method for producing an optically active alcohol of the present invention.

The reaction conditions of the method for producing an optically active alcohol of the present invention are not particularly limited. The reaction time is usually in the range from 6 to 48 hours, preferably from 12 to 36 hours, more preferably from 18 to 24 hours. The reaction temperature is usually in the range from 0° C. to 70° C., preferably from 10° C. to 50° C., more preferably from 15° C. to 40° C., and further preferably from 20° C. to 30° C.

The production of an optically active alcohol of the present invention may be performed in the presence or absence of a solvent. The method is preferably performed in the absence of a solvent because an optically active alcohol can be obtained with a high yield. Moreover, this method is preferably performed in the presence of a solvent because a solid carbonyl compound such as a solid ketone compound, and the like can be used as a starting material. Examples of the solvent include hexane, heptane and toluene. The solvent may be used singly or in combination of two or more types thereof. The solvent may further contain an alcohol such as methanol and ethanol for the improvement of the yield.

A titanium additive such as Ti(Oi-Pr)$_4$ is not necessarily used as a reaction accelerator in the method for an optically active alcohol of the present invention. Conventionally, an equimolar or excess amount of the titanium additive was used as a reaction accelerator. However, such a titanium additive is not easy to handle because of strong moisture-absorption resolvability. Since the titanium additive is not necessarily used in the present invention, the production of an optically active alcohol can be readily performed. Of course, such a titanium additive may be used in the present invention. However, the amount of the titanium additive used can be 2 equivalents or less, preferably 1 equivalent or less, more preferably 0.5 equivalent or less, further preferably 0.3 equivalent or less, and particularly 0.1 equivalent or less.

An alkyne can be further mixed in the method for the production of an optically active alcohol of the present invention. When an alkyne is mixed, an alkynyl group derived from the alkyne can be added to the above-mentioned carbonyl compound such as an aldehyde and a ketone. This is presumably because an alkynyl zinc generated by reaction of the added organozinc compound with the above-mentioned alkyne is coordinated to the ligand of the present invention, forming a complex, followed by reaction of the complex with the above-mentioned carbonyl compound (note that this consideration is the inventor's presumption; therefore, this conclusion is not intended to limit the scope of the present invention). That is, the organic group in the organozinc compound may be the same as or different from the organic group added to the above-mentioned carbonyl compound in the method for the production of an optically active alcohol of the present invention.

The type and structure of the optically active alcohol obtained by the present invention are not particularly limited. Not only an asymmetric alkylation reaction but also an asymmetric phenylation reaction is possible in the method for the production of an optically active alcohol of the present invention. Moreover, various organozinc compounds can be used in the method for the production of an optically active alcohol of the present invention. As a result, various kinds of optically active alcohols having various structures can be produced.

EXAMPLE

Hereinafter, the present invention is specifically described using Examples, however, the present invention is not limited to the embodiments by Examples. The embodiments in the present invention can be varied in the range thereof according to the purpose, application and the like.

<A> Synthesis of Optically Active Tertiary Alcohol Using Phosphoramide Compound (1) Synthesis of Phosphoramide Compound Phosphoramide compounds (L1) and (L2) represented by the following chemical formulae were synthesized according to the method below. The structures of the phosphoramide compounds (L1) and (L2) and their synthetic schemes are as follows.

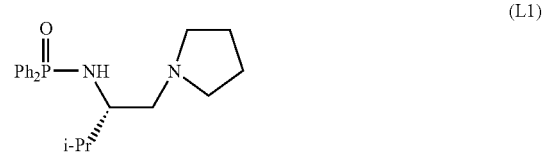

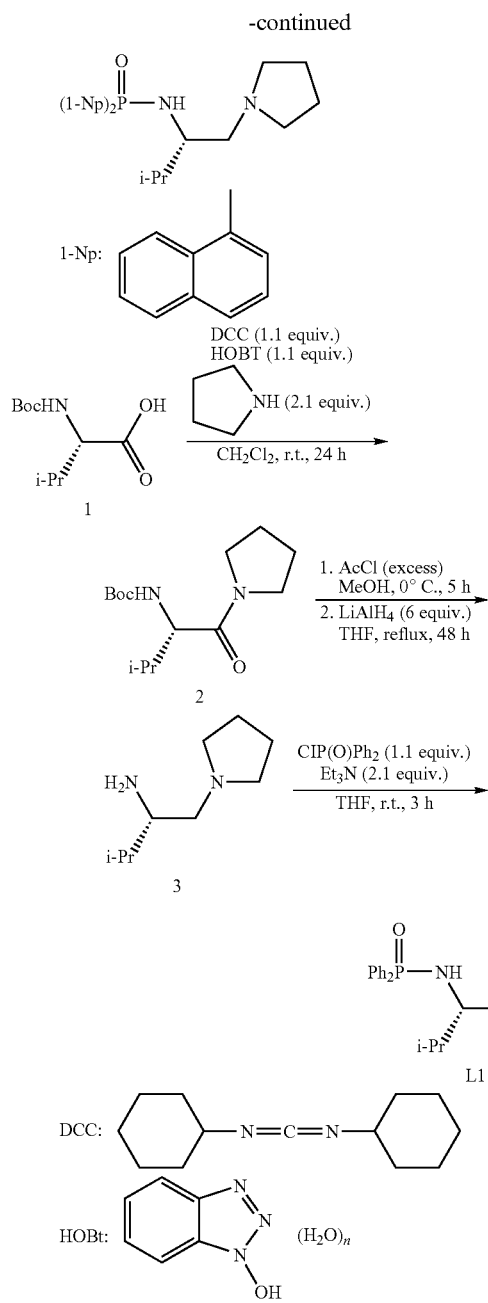

<Synthesis of Amide (2) Using Amino Acid Derivative (1)>

100 ml of dehydrated methylene chloride was added to a reaction vessel containing 4.25 g (20.0 mmol) of an amino acid derivative (1) under a nitrogen atmosphere to dissolve the amino acid derivative (1). 4.54 g (22.0 mmol) of dicyclohexylcarbodiimide (DCC) and 2.97 g (22.0 mmol) of 1-hydroxybenzotriazole (HOBt) were then added. The above-mentioned amino acid derivative (1) is an amino acid derivative in which the nitrogen atom of L-valine is protected with a tert-butoxycarbonyl group (Boc).

Subsequently, the solution was cooled to 0° C., and 3.67 ml (44.0 mmol) of pyrrolidine was added dropwise over 10 minutes. After dropping, the mixture was stirred at 0° C. for 15 minutes, and warmed to room temperature, followed by further stirring for 24 hours.

The completion of the reaction was confirmed by a TLC, and the mixture was cooled to 0° C. After that, 20 ml of a 10% citric acid aqueous solution was added and stirred for 10 minutes, followed by warming to room temperature. Extraction from the mixture was performed twice using 50 ml of chloroform. The extracted organic layer was washed with 20 ml of a 10% citric acid aqueous solution and 20 ml of a saturated sodium chloride aqueous solution, and dried with magnesium sulfate. The extracted organic layer was filtered using "Celite" (trade name), and the solvent was distilled off under reduced pressure. The obtained concentrated liquid was purified by passing through silica gel column chromatography (hexane/ethyl acetate=(3/1) to (1/1)), and thus amide (2) was obtained. The yield of the amide (2) was 82% (4.43 g).

<Synthesis of Diamine (3) Using Amide (2)>

Methanol was added to a reaction vessel containing the obtained amide (2) to dissolve the amide (2), and the solution was cooled to 0° C. 20 ml of acetyl chloride was added dropwise to the mixture over 10 minutes. After dropping, the mixture was stirred at 0° C. for 3 hours, warmed to room temperature, and further stirred for 1 hour. Subsequently, the solvent was distilled off under reduced pressure, and Boc-deprotected amine was obtained quantitatively. The Boc-deprotected amine was used in the next reaction without purification.

3.8 g (100 mmol) of lithium aluminum hydride was added to a reaction vessel equipped with a reflux condenser under a nitrogen atmosphere. After the reaction vessel was cooled to 0° C., 100 ml of dehydrated tetrahydrofuran (THF) was added. Then, 50 ml of the obtained tetrahydrofuran solution containing the Boc-deprotected amine was added dropwise over 10 minutes into the mixture. After dropping, the reaction mixture was stirred at 0° C. for 30 minutes and then refluxed for 48 hours.

The completion of the reaction was confirmed by a TLC, and the mixture was cooled to 0° C. 10 g of sodium sulfate and 20 ml of water were carefully added dropwise while vigorously stirring the mixture. After dropping, the mixture was stirred at 0° C. for 30 minutes and filtered using "Celite" (trade name). The residue was washed with diethyl ether, and then the collected organic layer was distilled off under reduced pressure. The obtained concentrated liquid was purified by passing through basic silica gel column chromatography (hexane/ethyl acetate=(3/1) to (1/1)), and thus diamine (3) was obtained. The yield of the diamine (3) was 61% (1.56 g).

<Synthesis of Phosphoramide Compound (L1) Using Diamine (3)>

20 ml of tetrahydrofuran was added to a reaction vessel containing the diamine (3) under a nitrogen atmosphere. 2.22 g (22.0 mmol) of triethylamine was then added, and the reaction vessel was cooled to 0° C. After cooling, 2.60 g (11.0 mmol) of diphenylphosphinic acid chloride was added dropwise over 5 minutes. After dropping, the mixture was stirred at 0° C. for 30 minutes, warmed to room temperature, and further stirred for 3 hours. The completion of the reaction was confirmed by a TLC, and the mixture was cooled to 0° C. Subsequently, 10 ml of water was added and warmed to room temperature. Extraction from the mixture was performed twice using 20 ml of chloroform. The extracted organic layer was washed with 10 ml of a saturated sodium chloride aqueous solution, and dried with magnesium sulfate. The filtration was performed using "Celite" (trade name) and the solvent was distilled off under reduced pressure. The obtained concentrated liquid was purified by passing through basic silica gel column chromatography (hexane/ethyl acetate=(3/1) to (1/1)), and thus the phosphoramide compound (L1) was obtained. The yield of the phosphoramide compound (L1) was 86% (3.06 g).

The spectrum data of the phosphoramide compound (L1) was as follows:

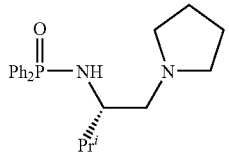

(S)—N-(3-Methyl-1-(1-pyrrolidinyl)-2-butanyl) diphenylphosphinic Amide (L1)

$^1$H NMR (300 MHz, CDCl$_3$) δ0.84 (d, J=6.3 Hz, 3H), 0.91 (d, J=6.3 Hz, 3H), 1.68-1.78 (m, 4H), 1.97 (m, 1H), 2.41-2.56 (m, 4H), 2.63-2.73 (m, 1H), 3.31 (m, 1H), 3.46 (br, 1H), 7.38-7.50 (m, 6H), 7.85-7.95 (m, 4H).

$^{13}$C NMR (75 MHz, CDCl$_3$) δ17.6 (CH$_3$), 18.2 (CH$_3$), 23.5 (CH$_2$), 30.3 (CH), 54.3 (CH$_2$), 55.1 (CH), 57.5 (d, J=5.7 Hz, CH), 128.2, 128.4, 131.6, 132.0, 132.1, 132.2.

$^{31}$P NMR (121 MHz, CDCl$_3$) δ 23.9 (s, 1P). IR (KBr) 3158, 2957, 2777, 1590, 1458, 1354, 1283, 1179, 1107, 1049, 974 cm$^{-1}$.

$[α]_D^{20}$=-9.2 (c 1.00, THF).

The phosphoramide compound (L2) was synthesized in the same manner as above.

$^{31}$P-NMR (121 MHz) of the phosphoramide compound (L1) was measured in methylene chloride. Next, one equivalent of diethylzinc was added to the phosphoramide compound (L1), and $^{31}$P-NMR (121 MHz) was measured.

As a result, the phosphoramide compound (L1) gave a singlet peak at 22.20 ppm. When one equivalent of diethylzinc was added to this solution, a new singlet peak was observed at 23.38 ppm, accompanied by the generation of one equivalent of ethane gas.

(2) Synthesis of Optically Active Tertiary Alcohol (I)—Ethylation Reaction of Ketone The phosphoramide compounds (L1) and (L2) were used as a ligand. These ligands were added to react acetophenone with diethylzinc and an optically active tertiary alcohol was synthesized.

3.0 ml (3.0 mmol) of diethylzinc (1.0 M heptane solution) was added to a Schlenk reaction flask containing 45.6 mg (0.10 mmol) of the phosphoramide compound (L2) under a nitrogen atmosphere, and stirred at room temperature for 30 minutes. Subsequently, 120.2 mg (1.0 mmol) of acetophenone was added to the reaction mixture, and stirred at room temperature for 24 hours.

The completion of the reaction was confirmed by a TLC. After confirmation, the mixture was cooled to 0° C. 10 ml of a saturated aqueous ammonium chloride solution was then added and warmed to room temperature. Extraction from the mixture was performed twice using 15 ml of diethyl ether. The extracted organic layer was washed with 10 ml of a saturated sodium chloride aqueous solution, and dried with magnesium sulfate. Then, the filtration was performed using "Celite" (trade name), and the solvent was distilled off under reduced pressure.

The obtained concentrated liquid was purified by passing through silica gel column chromatography (pentane/diethyl ether=(10/1) to (2/1)), and thus an optically active tertiary alcohol was obtained. The yield was 80% (120.1 mg). Further, the enantiomeric excess of the obtained optically active tertiary alcohol was measured by gas chromatography using a chiral column. As a result, the enantiomeric excess was 93% ee (S).

An optically active tertiary alcohol was synthesized in the same manner as above except that the phosphoramide compound (L1) was used as a ligand instead of the phosphoramide compound (L2), and that the reaction temperature was room temperature. As a result, the yield was 21%, and the enantiomeric excess was 87% ee (S). Meanwhile, an optically active tertiary alcohol was synthesized in the same manner as above except that the reaction temperature was changed from room temperature to 50° C. As a result, the yield was 32%, and the enantiomeric excess was 78% ee (S).

The following optically active tertiary alcohols were synthesized using the phosphoramide compounds (L1) and (L2) as a ligand in the same manner as above. The structure of the synthesized optically active tertiary alcohols, the reaction time (h), yield (%), and enantiomeric excess (% ee) are indicated below.

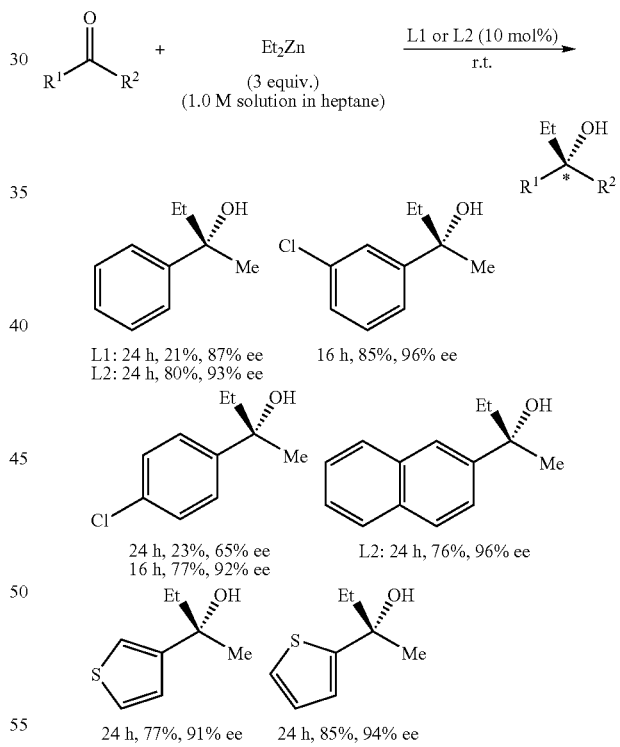

(3) Synthesis of Optically Active Tertiary Alcohol (II)—Phenylation Reaction of Ketone 1.0 ml (3.0 mmol) of diphenylzinc (1.0 M heptane solution) and 2.0 ml (2.0 mmol) of diethylzinc (1.0 M heptane solution) were used instead of the diethylzinc in the method of synthesizing optically active tertiary alcohols described in Section (2). Other conditions were the same as in the synthesis method of Section (2), and p-chloroacetophenone, diphenylzinc, and diethylzinc were reacted to synthesize an optically active tertiary alcohol.

The following optically active tertiary alcohols were synthesized in the same manner as above. The structure of the synthesized optically active tertiary alcohols, the reaction time (h), yield (%), and enantiomeric excess (% ee) are indicated below.

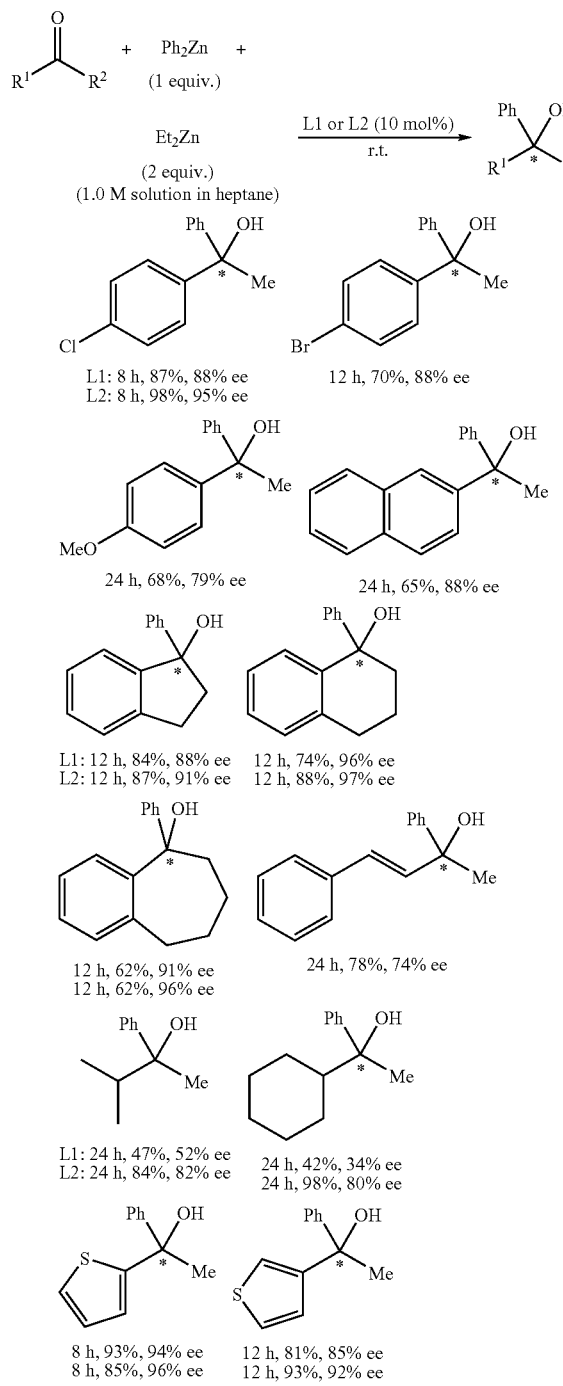

Further, optically active tertiary alcohols were synthesized in the same manner as above except that the amount of the ligand and the reaction temperature were changed. The results are shown below.

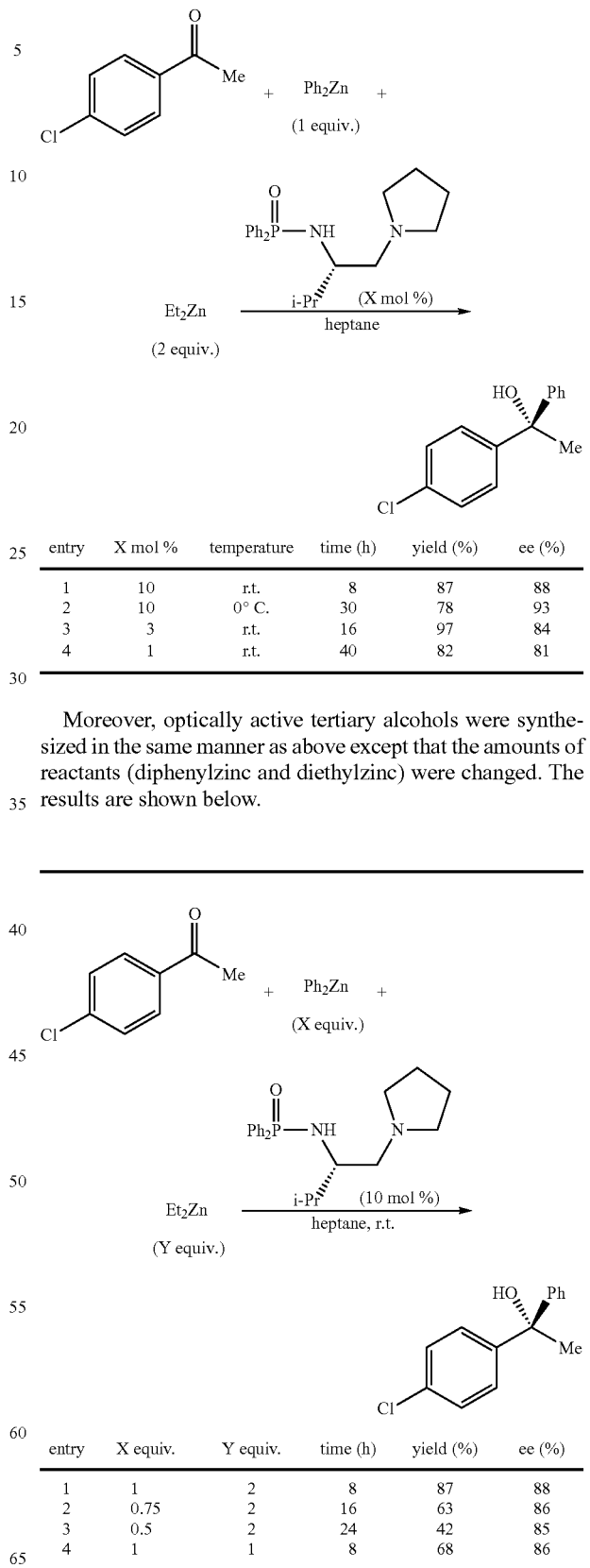

| entry | X mol % | temperature | time (h) | yield (%) | ee (%) |
|---|---|---|---|---|---|
| 1 | 10 | r.t. | 8 | 87 | 88 |
| 2 | 10 | 0° C. | 30 | 78 | 93 |
| 3 | 3 | r.t. | 16 | 97 | 84 |
| 4 | 1 | r.t. | 40 | 82 | 81 |

Moreover, optically active tertiary alcohols were synthesized in the same manner as above except that the amounts of reactants (diphenylzinc and diethylzinc) were changed. The results are shown below.

| entry | X equiv. | Y equiv. | time (h) | yield (%) | ee (%) |
|---|---|---|---|---|---|
| 1 | 1 | 2 | 8 | 87 | 88 |
| 2 | 0.75 | 2 | 16 | 63 | 86 |
| 3 | 0.5 | 2 | 24 | 42 | 85 |
| 4 | 1 | 1 | 8 | 68 | 86 |

(4) Synthesis of Optically Active Tertiary Alcohol (III)

The following phosphoramide compounds were synthesized in the same manner as in Section (1). The obtained phosphoramide compounds were used as a ligand instead of the phosphoramide compounds (L1) and (L2) in the method of synthesizing optically active tertiary alcohols described in Section (2). Other conditions were the same as in the method of Section (2), and optically active tertiary alcohols were synthesized in the same manner as in above (2). The structure of the synthesized phosphoramide compounds, the reaction time, yield, and enantiomeric excess are indicated below.

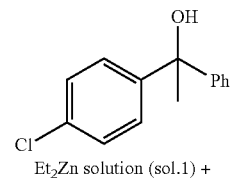

| Ligand | Time(h)/Yield(%)/ee(%) Et₂Zn solution (sol.1) + solvent (sol. 2) | only Et₂Zn solution |
|---|---|---|
| Ph₂P(O)—NH—CH(Pr$^i$)—CH₂—N(pyrrolidine, 5) | 24/53/80 (hep + hep) | 8/94/81 (hex)<br>6/65/86 (tol)<br>8/87/88 (hep) |
| Ph₂P(O)—NH—CH(Pr$^i$)—CH₂—N(piperidine, 6) | 24/61/64 (hex + hex)<br>24/24/74 (tol + hex) | |
| Ph₂P(O)—NH—CH(Pr$^i$)—CH₂—N(morpholine) | 24/48/68 (hex + hex) | |
| Ph₂P(O)—NH—CH(Pr$^i$)—CH₂—N(azepane, 7) | 24/38/85 (hex + hex) | |
| Ph₂P(O)—NH—CH(Pr$^i$)—CH₂—NMe₂ | 24/30/80 (hep + hep) | |
| Ph₂P(O)—NH—CH(Bn)—CH₂—N(pyrrolidine, 5) | 24/44/78 (hep + hep) | 8/98/82 (hep) |
| Ph₂P(O)—NH—CH(Bn)—CH₂—N(piperidine, 6) | 24/52/77 (hex + hex) | |

-continued
| Ligand Time(h)/Yield(%)/ee(%) | 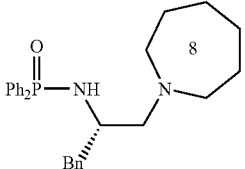 Et₂Zn solution (sol.1) + solvent (sol. 2) | 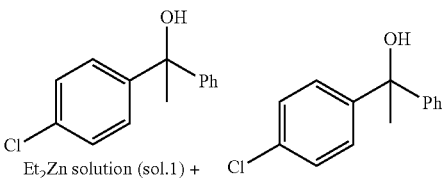 only Et₂Zn solution |
|---|---|---|
| 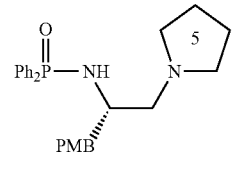 | 24/68/82 (hex + hex) | |
| 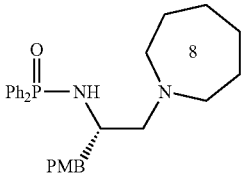 | | 8/86/83 (hep) |
| 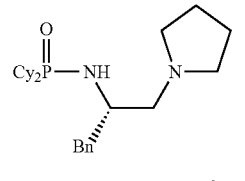 | 24/93/78 (hex + hex) | |
| 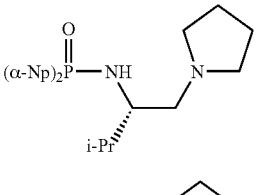 | 24/42/77 (hep + hep) | |
| 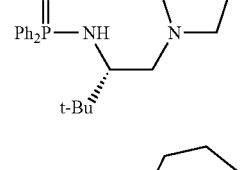 | | 8/98/95 (hep) |
| 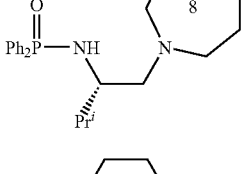 | | 12/45/58 (hep) |
| 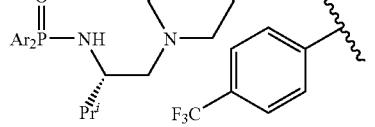 | 24/46/86 (hex + hex) | |
| 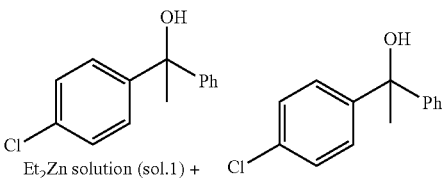 | 24/31/65 (hex + hex) | |

| Ligand<br>Time(h)/Yield(%)/ee(%) | Et$_2$Zn solution (sol.1) +<br>solvent (sol. 2) | only Et$_2$Zn solution |
|---|---|---|
| 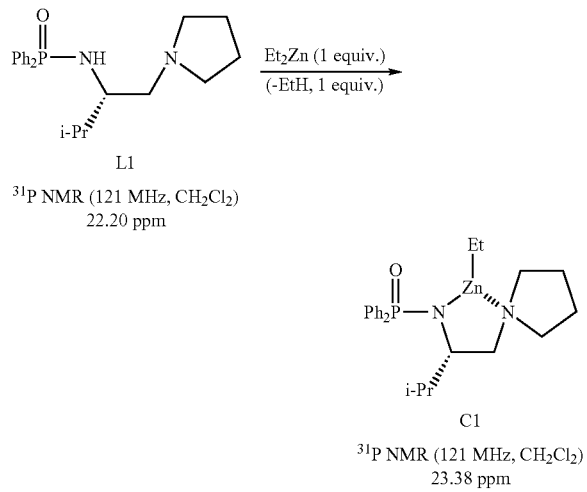 | 24/51/74 (hex + hex) | |

(5) Results of Examples

It is found from the spectrum data of the phosphoramide compound (L1) and the generation of one equivalent of ethane gas, that the phosphoramide compound (L1) and diethylzinc form a zinc complex.

Moreover, this result suggests that the zinc complex is presumably one represented by the general formula (C1) formed by the following scheme (note that this consideration is the inventor's presumption; therefore, this conclusion is not intended to limit the scope of the present invention).

Although optically active tertiary alcohols were conventionally difficult to synthesize, they can be synthesized with a high efficiency and high enantioselectivity by using the phosphoramide compounds (L1) and (L2). In addition, optically active tertiary alcohols can be synthesized with a high efficiency and high enantioselectivity, without the addition of conventionally used reactants such as titanium additives.

Comparing the phosphoramide compounds (L1) and (L2), the yield as well as the enantiomeric excess is higher when the phosphoramide compound (L2) is used. Accordingly, optically active tertiary alcohols can be synthesized with a high efficiency and high enantioselectivity by using the phosphoramide compound (L2).

Additionally, various phosphoramide compounds of the present invention were synthesized, and the alkyl addition reaction of a ketone was performed using these phosphoramide compounds as a ligand. As a result, tertiary alcohols were synthesized with a high enantioselectivity using any of these ligands.

<B> Synthesis of Optically Active Secondary Alcohol Using Phosphoramide Compound (1) Synthesis of Ligand Ligands (L3) to (L12) represented by the following chemical formulae were synthesized in the following manner. The structures of the ligands (L3) to (L12) and their synthetic schemes are as follows.

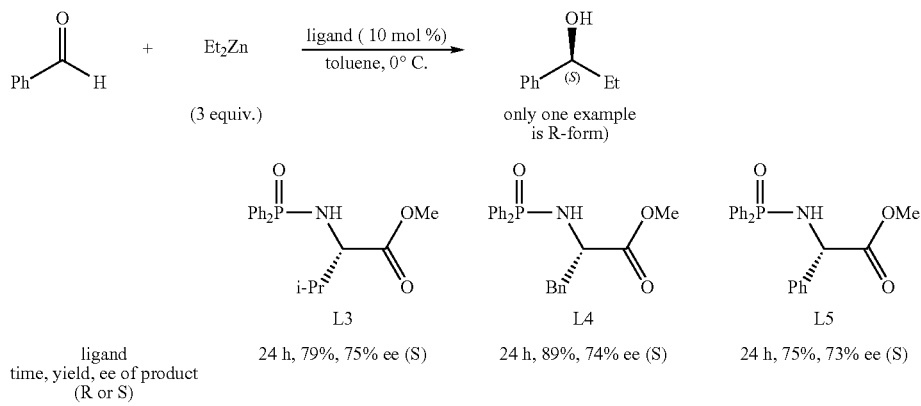

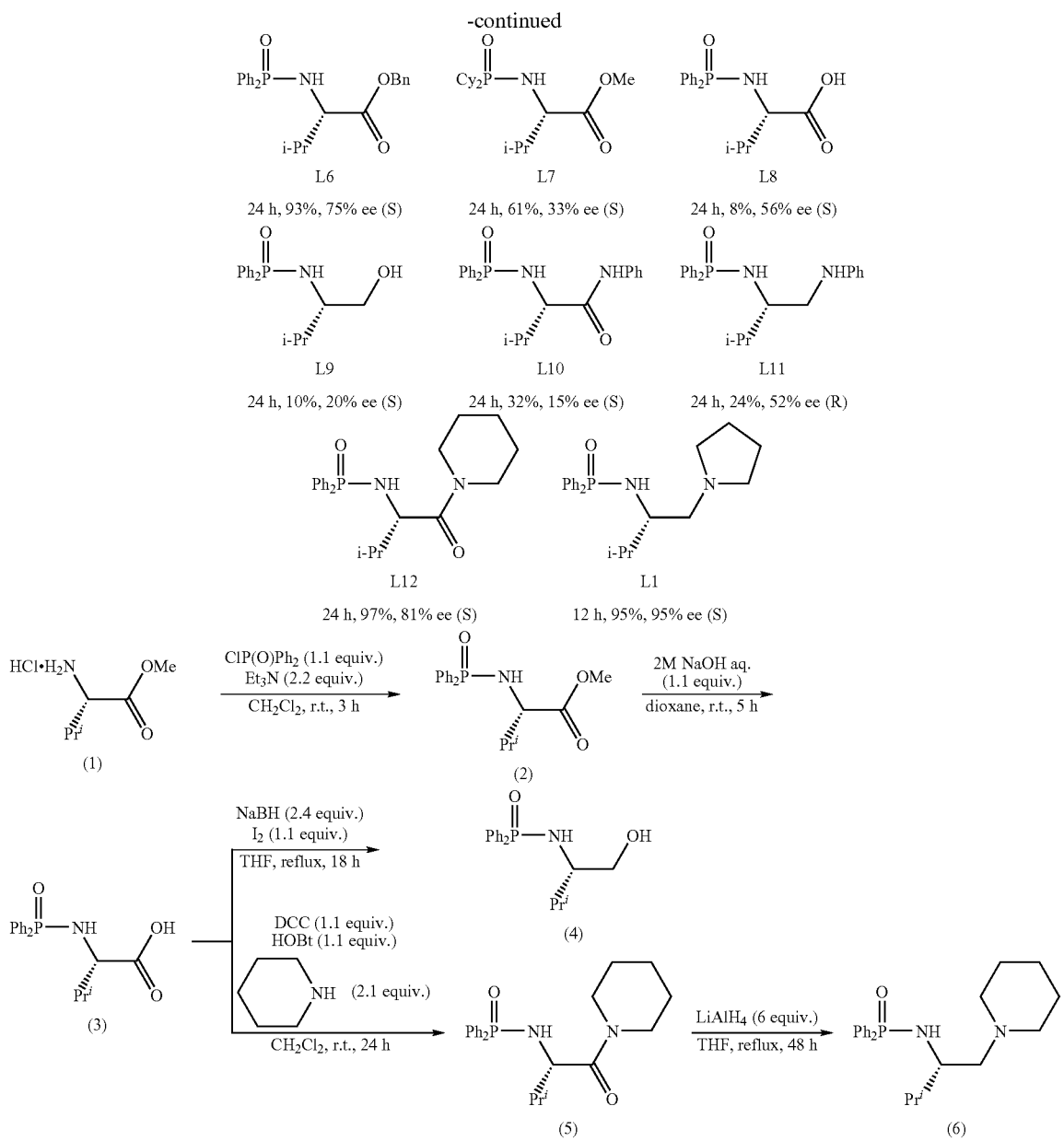

<Synthesis of Phosphoramide (2) Using Amino Acid Hydrochloride (1)>

50 ml of methylene chloride was added to a reaction vessel containing 3.35 g (20 mmol) of an amino acid hydrochloride (1) under a nitrogen atmosphere. 4.44 g (22 mmol) of triethylamine was then added, and the reaction vessel was cooled to 0° C. After cooling, 5.20 g (22 mmol) of diphenylphosphinic acid chloride was added dropwise over 5 minutes. After dropping, the mixture was stirred at 0° C. for 30 minutes, warmed to room temperature, and further stirred for 3 hours. The completion of the reaction was confirmed by a TLC, and the mixture was cooled to 0° C. 20 ml of water was added and then the mixture was warmed to room temperature. Extraction from the mixture was performed twice using 30 ml of chloroform. The extracted organic layer was washed with 20 ml of a saturated sodium chloride aqueous solution, and was dried with magnesium sulfate. The filtration was performed using "Celite" (trade name), and the solvent was distilled off under reduced pressure. The obtained concentrated liquid was purified by passing through silica gel column chromatography (hexane/ethyl acetate=(3/1) to (1/1)), and thus phosphoramide (2) was obtained. The yield of the phosphoramide (2) was 68% (4.51 g).

<Synthesis of Carboxylic Acid (3) Using Ester (2)>

20 ml of 1,4-dioxane was added to a reaction vessel containing 3.31 g (10 mmol) of the obtained phosphoramide (2). The solution was then cooled to 0° C., and 5.5 ml of 2M sodium hydroxide aqueous solution was added dropwise over 10 minutes. After dropping, the mixture was stirred at 0° C. for 15 minutes, warmed to room temperature, and further stirred for 5 hours. The completion of the reaction was confirmed by a TLC, and the mixture was cooled to 0° C. Subsequently, a saturated citric acid aqueous solution was added to adjust the pH of the mixture between 3 and 4. Extraction from the mixture was performed twice using 30 ml of ethyl acetate. The extracted organic layer was washed with 20 ml of water and 20 ml of a saturated sodium chloride aqueous solution, and dried with magnesium sulfate. The filtration was performed using "Celite" (trade name), and the solvent was distilled off under reduced pressure. The obtained crude product was recrystallized using a solvent in which hexane and toluene were mixed at a ratio of 1:1, and thus a carboxylic acid (3) was obtained. The yield of the carboxylic acid (3) was 99% or more (3.17 g).

<Synthesis of Alcohol (4) Using Carboxylic Acid (3)>

908 mg (24 mmol) of sodium borohydride was added to a reaction vessel equipped with a reflux condenser under a nitrogen atmosphere. The reaction vessel was cooled to 0° C., and then 30 ml of dehydrated tetrahydrofuran (THF) was added. Next, 20 ml of a tetrahydrofuran solution containing 3.17 g (10 mmol) of the above-mentioned carboxylic acid (3) was added into the vessel at once. 10 ml of a tetrahydrofuran solution containing 2.54 g (10 mmol) of iodine was then added dropwise to the mixture over 10 minutes. After dropping, the reaction mixture was stirred at 0° C. for 15 minutes and then refluxed for 18 hours. The completion of the reaction was confirmed by a TLC, and the mixture was cooled to 0° C. Then, methanol was carefully added dropwise until the reaction mixture became homogenized. After the dropping was completed, the mixture was stirred at 0° C. for 30 minutes, and the solvent was distilled off under reduced pressure. 20 ml of a 20% potassium hydroxide aqueous solution was added to the obtained concentrated liquid. After the mixture was stirred at room temperature for 4 hours, extraction was performed twice using 50 ml of chloroform. The extracted organic layer was washed with 20 ml of water and 20 ml of a saturated sodium chloride aqueous solution, and dried with magnesium sulfate. The filtration was performed using "Celite" (trade name), and the solvent was distilled off under reduced pressure. The obtained concentrated liquid was purified by passing through silica gel column chromatography (hexane/ethyl acetate=(3/1) to (1/1)), and thus an alcohol (4) was obtained. The yield of the alcohol (4) was 47% (1.42 g).

<Synthesis of Amide (5) Using Carboxylic Acid (3)>

50 ml of dehydrated methylene chloride was added to a reaction vessel containing 3.17 g (10 mmol) of the obtained carboxylic acid (3) under a nitrogen atmosphere to dissolve the acid. Subsequently, 2.27 g (11 mmol) of DCC and 1.48 g (11 mmol) of HOBt were then added. The mixture was then cooled to 0° C., and 2.17 ml (22 mmol) of piperidine was added dropwise over 10 minutes. After dropping, the mixture was stirred at 0° C. for 15 minutes, warmed to room temperature, and further stirred for 24 hours. The completion of the reaction was confirmed by a TLC, and the mixture was cooled to 0° C. After 10 ml of a 10% citric acid aqueous solution was added, the mixture was stirred for 10 minutes and warmed to room temperature. Extraction from the mixture was performed twice using 30 ml of chloroform. The extracted organic layer was washed with 10 ml of a 10% citric acid aqueous solution and 10 ml of a saturated sodium chloride aqueous solution, and dried with magnesium sulfate. The filtration was performed using "Celite" (trade name), and the solvent was distilled off under reduced pressure. The obtained concentrated liquid was purified by passing through silica gel column chromatography (hexane/ethyl acetate=(3/1) to (1/1)), and thus an amide (5) was obtained. The yield of the amide (5) was 62% (2.38 g).

<Synthesis of Amine (6) Using Amide (5)>

152 g (40 mmol) of lithium aluminum hydride was added to a reaction vessel equipped with a reflux condenser under a nitrogen atmosphere. The reaction vessel was cooled to 0° C., and then 40 ml of dehydrated tetrahydrofuran (THF) was added. Subsequently, 20 ml of the tetrahydrofuran solution containing the obtained amide (5) was added dropwise over 10 minutes. After dropping, the reaction mixture was stirred at 0° C. for 30 minutes and then refluxed for 48 hours. The completion of the reaction was confirmed by a TLC, and the mixture was cooled to 0° C. Then, 4 g of sodium sulfate and 10 ml of water were carefully added dropwise while vigorously stirring the mixture. After dropping, the mixture was stirred at 0° C. for 30 minutes and filtered using "Celite" (trade name). The residue was washed with diethyl ether, and the collected organic layer was distilled off under reduced pressure. The obtained concentrated liquid was purified by passing through basic silica gel column chromatography (hexane/ethyl acetate=(3/1) to (1/1)), and thus an amine (6) was obtained. The yield of the amine (6) was 57% (1.30 g).

(2) Synthesis of Optically Active Secondary Alcohol

The phosphoramide compound (L1) and the ligands (L3) to (L12) were used as a ligand. Each of these ligands was added, and benzaldehyde and diethylzinc were reacted to synthesize an optically active secondary alcohol.

3.0 ml (3.0 mmol) of diethylzinc (1.0 M toluene solution) was added to a Schlenk reaction tube containing 0.10 mmol of the phosphoramide compound (L1) or the ligands (L3) to (L12) under a nitrogen atmosphere, and stirred at 0° C. for 30 minutes. Then, 1.0 mmol of benzaldehyde was added to the reaction solution and stirred at 0° C. for 24 hours.

The completion of the reaction was confirmed by a TLC. After confirmation, 10 ml of a saturated aqueous ammonium chloride solution was added and warmed to room temperature. Extraction from the mixture was performed twice using 15 ml of diethyl ether. The extracted organic layer was washed with 10 ml of a saturated sodium chloride aqueous solution, and dried with magnesium sulfate. Then, the filtration was performed using "Celite" (trade name), and the solvent was distilled off under reduced pressure.

The obtained concentrated liquid was purified by passing through silica gel column chromatography (pentane/diethyl ether=(10/1) to (2/1)), and thus an optically active secondary alcohol was obtained. The structure of the synthesized optically active secondary alcohol, the reaction time, yield, and enantiomeric excess are indicated together with the structure of each of the above ligands.

Optically active secondary alcohols can be synthesized from an aldehyde compound by using the phosphoramide compound (L1) and the ligands (L3) to (L12). Moreover, optically active secondary alcohols can be synthesized with a high efficiency and high enantioselectivity, without the addition of conventionally used reactants such as titanium additives. The phosphoramide compound (L1) is effective in synthesis of both optically active secondary alcohols and optically active tertiary alcohols.

When the ligands (L3) to (L7) (ester) are used, higher yield and higher enantioselectivity are provided rather than when the ligand (L8) (carboxylic acid) and ligand (L9) (alcohol) are used. Moreover, when the ligands (L3) to (L6) are used, higher enantioselectivity is provided rather than when the ligand (L7) is used. Furthermore, when the ligand (L6) is used, higher yield is provided rather than when the ligand (L3) is used.

The ligand (L11) in which amide is reduced ensures higher enantioselectivity rather than the ligand (L10) having an amide structure. Moreover, the tertiary amine (L12) is superior to the secondary amine (L10) in both the yield and enantioselectivity.

INDUSTRIAL APPLICABILITY

The present invention is useful for synthesizing an optically active alcohol from a carbonyl compound such as an aldehyde compound and ketone compound, particularly a ketone compound, with a high efficiency and high enantioselectivity. The optically active alcohol synthesized by the present invention is useful as drugs and pesticides, or synthetic intermediates thereof. For example, drugs (e.g., clemastine that is often used as an antihistamine) can be synthesized without an optical resolution process, which was essential in the past, by using the optically active alcohols synthesized by the present invention.

What is claimed is:

1. A method for producing an optically active alcohol, comprising:
    reacting a carbonyl compound with an organozinc compound in the presence of a phosphoramide compound,
    wherein the carbonyl compound is one of an aldehyde compound and a ketone compound,
    wherein the organozinc compound comprises a compound represented by general formula (11) or compounds represented by general formulae (12) and (13), ZnR$^{10}$R$^{11}$     (11)

ZnR$^{12}$R$^{13}$     (12)

ZnR$^{14}$R$^{15}$     (13)

wherein
    R$^{10}$ and R$^{11}$ independently are monovalent hydrocarbon groups, and at least one of R$^{10}$ and R$^{11}$ is an alkyl group, alkenyl group or alkynyl group;
    R$^{12}$ and R$^{13}$ independently are aryl group, arylalkyl group or arylalkenyl group; and
    R$^{14}$ and R$^{15}$ independently are alkyl group, alkenyl group or alkynyl group, and the phosphoramide compound is represented by general formula (1) or (1')

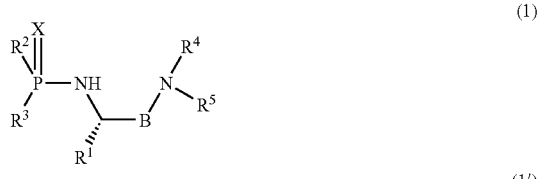

(1)

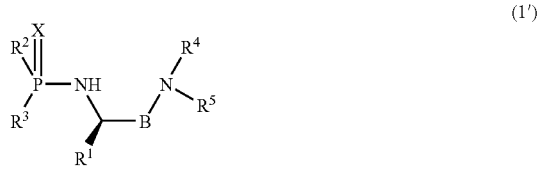

(1')

wherein
    R$^1$ is an alkyl group having 1 to 8 carbon atoms, a phenyl group or an optionally substituted benzyl group;
    R$^2$ and R$^3$ independently are a phenyl group, a naphthyl group, a cyclohexyl group or an aryl group having 6 to 15 carbon atoms that may have a substituent;
    R$^4$ and R$^5$ independently are an alkyl group having 1 to 8 carbon atoms or may be bonded together to form a five-to-eight membered saturated ring with a nitrogen atom to which R$^4$ and R$^5$ are attached, where the ring may have a hetero atom in the ring;
    X is an oxygen atom; and
    B is a methylene group or carbonyl group.

2. The method for producing an optically active alcohol according to claim 1, wherein said phosphoramide compound is added in an amount in the range from 0.1% to 20% by mol based on said carbonyl compound.

3. The method for producing an optically active alcohol according to claim 1, wherein said carbonyl compound is a ketone compound represented by general formula (14) or (15):

(14)

(15)

wherein
    R$^{16}$ is a monovalent hydrocarbon group having three or more carbon atoms;
    R$^{17}$ is a monovalent hydrocarbon group different from R$^{16}$;
    n is an integer of two or more; and
    the aromatic ring of the general formula (15) may have a substituent.

4. The method for producing an optically active alcohol according to claim 1, wherein an equivalent ratio of said organozinc compound represented by general formula (12) to said organozinc compound represented by general formula (13) is 1:(1 to 5).

5. A method for producing an optically active alcohol, comprising:
    reacting a carbonyl compound with an organozinc compound in the presence of a ligand,
    wherein the carbonyl compound is one of an aldehyde compound and a ketone compound,
    wherein the organozinc compound comprises a compound represented by general formula (11) or compounds represented by general formulae (12) and (13), ZnR$^{10}$R$^{11}$     (11)

ZnR$^{12}$R$^{13}$     (12)

ZnR$^{14}$R$^{15}$     (13)

wherein
    R$^{10}$ and R$^{11}$ independently are monovalent hydrocarbon groups, and at least one of R$^{10}$ and R$^{11}$ is an alkyl group, alkenyl group or alkynyl group;
    R$^{12}$ and R$^{13}$ independently are aryl group, arylalkyl group or arylalkenyl group; and
    R$^{14}$ and R$^{15}$ independently are alkyl group, alkenyl group or alkynyl group, and the ligand is represented by general formula (8a), (8b), (9a) or (9b):

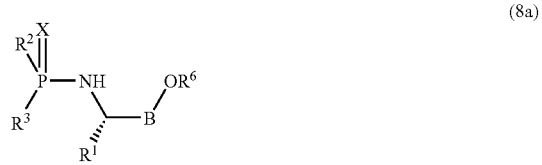

(8a)

-continued

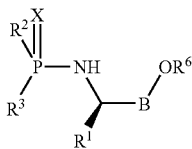
(8b)

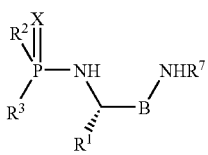
(9a)

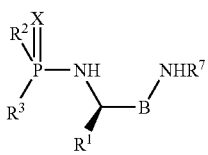
(9b)

wherein
$R^1$ to $R^3$ and $R^7$ independently are monovalent hydrocarbon groups;
$R^2$ and $R^3$ are each bound to a phosphorus atom directly or via an atom other than carbon atom;
$R^6$ is a hydrogen atom or a monovalent hydrocarbon group;
X is an oxygen atom or sulfur atom; and
B is a methylene group or carbonyl group.

6. The method according to claim 5, wherein said reacting is performed in the presence of a complex comprising the ligand and a zinc atom.

7. The method according to claim 6, for wherein said reacting is performed in the presence of a catalyst comprising the complex.

8. The method according to claim 1, wherein the reacting is performed in the presence of a complex or a catalyst comprising the complex, and the complex comprises the phosphoramide compound and a zinc atom.

9. The method according to claim 1, wherein the carbonyl compound is an aldehyde compound.

10. The method according to claim 1, wherein the carbonyl compound is a ketone compound.

11. The method according to claim 1, wherein $R^2$ and $R^3$ independently are an alkoxyphenyl group or a halogenated alkylphenyl group.

12. The method according to claim 5, wherein the carbonyl compound is an aldehyde compound.

13. The method according to claim 5, wherein the carbonyl compound is a ketone compound.

* * * * *